United States Patent
Reed et al.

(10) Patent No.: US 7,794,961 B2
(45) Date of Patent: *Sep. 14, 2010

(54) SCREENING ASSAYS FOR AGENTS THAT ALTER INHIBITOR OF APOPTOSIS (IAP) PROTEIN REGULATION OF CASPASE ACTIVITY

(75) Inventors: John C. Reed, Rancho Santa Fe, CA (US); Quinn Deveraux, San Diego, CA (US); Guy S. Salvesen, Encinitas, CA (US); Ryosuke Takahashi, Tokyo (JP); Natalie Roy, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 425 days.

This patent is subject to a terminal disclaimer.

(21) Appl. No.: 11/651,651

(22) Filed: Jan. 9, 2007

(65) Prior Publication Data

US 2007/0128677 A1    Jun. 7, 2007

Related U.S. Application Data

(60) Continuation of application No. 09/799,994, filed on Mar. 5, 2001, now Pat. No. 7,192,728, which is a division of application No. 09/058,969, filed on Apr. 10, 1998, now Pat. No. 6,228,603.

(60) Provisional application No. 60/086,229, filed on May 22, 1997, now abandoned.

(51) Int. Cl.
    *G01N 33/574* (2006.01)
(52) U.S. Cl. .................................... 435/7.23; 435/7.21
(58) Field of Classification Search ........................ None
    See application file for complete search history.

(56) References Cited

U.S. PATENT DOCUMENTS

| 5,766,848 | A | 6/1998 | Borden et al. |
| 6,228,603 | B1 * | 5/2001 | Reed et al. .................... 435/18 |
| 7,192,728 | B2 * | 3/2007 | Reed et al. .................... 435/18 |

OTHER PUBLICATIONS

Ambrosini et al., "A novel anti-apoptosis gene, survivin, expressed in cancer and lymphoma," *Nature Medicine* 3:917-921 (1997).
Bertin et al., "Apoptotic Suppression by Baculovirus P35 Involves Cleavage by and Inhibition of a Virus-Induced CED-3/ICE-Like Protease," *Journal of Virology* 70:6251-6259 (1996).
Birnbaum et al., "An Apoptosis-Inhibiting Gene from a Nuclear Polyhedrosis Virus Encoding a Polypeptide with Cys/His Sequence Motifs," *Journal of Virology* 68:2521-2528 (1994).
Boldin et al., "Involvement of MACH, a Novel MORT1/FADD-Interacting Protease, in Fas/APO-1-and TNF Receptor-Induced Cell Death," *Cell* 85:803-815 (1996).
Bump et al., "Inhibition of ICE Family Proteases by Baculovirus Antiapoptotic Protein p35," *Science* 269:1885-1888 (1995).

Crystal, R.G., "Transfer of genes to humans; early lessons and obstacles to success," *Science* 270:404-410 (1995).
Crook et al., "An Apoptosis-Inhibiting Baculovirus Gene with a Zinc Finger-Like Motif," *Journal of Virology* 67:2168-2174 (1993).
Curti, B.D., "Physical barriers to drug delivery in tumors," *Crit. Rev. Oncol. Hematol.* 14:29-39 (1993).
Deonarain, M. P., "Ligand-targeted receptor-mediated vectors for gene delivery," *Expert. Opin. Ther. Pat.* 8:53-69 (1998).
Dermer, G.B., "Another anniversary for the war on cancer," *Bio/Tech.* 12:320 (1994).
Deveraux et al., "X-linked IAP is a direct inhibitor of cell-death proteases," *Nature* 388:300-304 (1997).
Drexler, H.G., "Recent results on the biology of Hidgkin and Reed-Sternberg cells. II. continuous cell lines," *Leuk. Lymphoma* 9:1-25 (1993).
Duckett et al., "A Conserved Family of Cellular Genes Related to the Baculovirus Iap Gene and Encoding Apoptosis Inhibitors," *EMBO J.*, 15:2685-2694 (1996).
Embleton et al. "Monoclonal antibodies to osteogenic sarcoma antigens" Monoclonal Antibodies and Cancer, Marcel Dekker, Inc. 23:181-207 (1984).
Freshney, R.I., Culture of animal cells, A manual of basic technique, Alan R. Liss, Inc., New York (1983), p. 3-4.
Gottschalk et al., "The ability of Bcl-x(L) and Bcl-2 to prevent apoptosis can be differentially regulated," *Cell Death and Differentiation* 3(1):113-118 (1996).
Gura, T. "Systems for identifying new drugs are often faulty," *Science* 278:1041-1042 (1997).
Gura, T., "Antisense has growing pains," *Science* 270:575-577 (1995).
Hartwell et al., "Integrating genetic approaches into the discovery of anticancer drugs," *Science* 278:1064-1068 (1997).

(Continued)

*Primary Examiner*—Sheela J Huff
(74) *Attorney, Agent, or Firm*—McDermott Will & Emery LLP

(57) ABSTRACT

The present invention relates to an action between an inhibitor of apoptosis (IAP) protein and members of the caspase family of cell death proteases, for example, an interaction of the X chromosome linked IAP (XIAP) and caspase-3, caspase-7 or caspase-9, wherein the IAP regulates the activity of the caspases. The invention provides screening assays for identifying agents that alter the specific association of an IAP such as XIAP, c-IAP-1 or c-IAP-2 and a caspase such as caspase-3 or caspase-7. The invention also provides screening assays for identifying agents that alter the specific association of an IAP such as XIAP, c-IAP-1 or c-IAP-2 and a pro-caspase such as pro-caspase-9. In addition, the invention also provides methods for identifying agents that modulate the activity of a caspase in the presence of an IAP and that regulate the activation of a pro-caspase by an IAP. The invention further provides methods of reducing the severity of a pathologic condition in an individual by administering to the individual an agent that alters the caspase inhibitory activity of an IAP. In addition, the invention provides methods of modulating the ability of a population of cells to survive ex vivo by contacting the cells with an agent that alters the caspase inhibitory activity of an IAP in the cells.

27 Claims, 8 Drawing Sheets

OTHER PUBLICATIONS

Hawkins et al., "Inhibition of interleukin 1.beta.-converting enzyme-mediated apoptosis of mammalian cells by baculovirus IAP," *Proc. Natl. Acad. Sci. USA* 93:13786-13790 (1996).

Hay et al., "*Drosophila* Homologs of Baculovirus Inhibitor of Apoptosis Proteins Function to Block Cell Death," *Cell* 83:1253-1262 (1995).

Hsu, T.C. "Karyotypes of cells in culture," Tissue Culture Methods and Applications, p. 764 Academic Press (1973).

Huang et al. "Cloning and characterization of an inhibitor of apoptosis protein (IAP) from *Bombyx mori*," *Biochim. Biophys. Acta.* 1499 (3):191-198 (2001).

Jacobson and Evan, "Breaking the ICE," *Current Biology* 4:337-340 (1994).

Jain, R.K. "Barriers to drug delivery in solid tumors," *Sci. Am*. Jul. 1994:271:58-65.

Kharbanda et al., "Role for Bcl-x.sub.L as an inhibitor of cytosolic cytochrome C accumulation in DNA damage-induced apoptosis," *Proc. Natl. Acad. Sci. USA* 94:6939-6942 (1997).

Kluck et al., "The Release of Cytochrome c from Mitochondria: A Primary Site for Bcl-2 Regulation of Apoptosis," *Science* 275:1132-1136 (1997).

Komiyama et al., "Inhibition of Interleukin-1.beta. Converting Enzyme by the Cowpox Virus Serpin CrmA," *J. Biol. Chem.* 269:19331-19337 (1994).

Kunkel et al., "Expression and localization of scatter factor/hepatocyte growth factor in human astrocytomas," *Neuro Oncol.* 3(2):82-88 (2001).

Li et al., "Cytochrome c and dATP-Dependent Formation of Apaf-1/Caspase-9 Complex Initiates and Apoptotic Protease Cascade," *Cell* 91:479-489 (1997).

Liston et al., "Suppression of apoptosis in mammalian cells by NAIP and a related family of IAP genes," *Nature* 379:349-353 (1996).

Liu et al., "Induction of apoptotic program in cell-free extracts: requirement for dATP and cytochrome c," *Cell* 86:147-157 (1996).

Martin and Green, "Protease Activation During Apoptosis: Death by a Thousand Cuts?," *Cell* 82:349-352 (1995).

Martin et al., "Cell-free reconstitution of Fas-, UV radiation- and ceramide-induced apoptosis," *EMBO J.* 14:5191-5200 (1995).

Miller and Vile, "Targeted vectors for gene therapy," *FASEB J.* 9:190-199 (1995).

Muzio et al., "FLICE Induced apoptosis in a cell-free system," *J. Biol. Chem.* 272:2952-2956 (1997).

Muzio et al., "FLICE, A Novel FADD-Homologous ICE/CED-3-like Protease, is Recruited to the CD95 (Fas/APO-1) Death-Inducing Signaling Complex," *Cell* 85:817-827 (1996).

Oltvai and Korsmeyer, "Checkpoints of dueling dimmers foil death wishes," *Cell* 79:189-192 (1994).

Orth and Dixit, "Bik and Bak Induce Apoptosis Downstream of CrmA but Upstream of Inhibitor of Apoptosis," *The Journal of Biological Chemistry* 272:8841-8844 (1997).

Orth et al., "Molecular ordering of apoptotic mammalian CED-3/ICE-like proteases," *J. Biol. Chem.* 271:20977-20980 (1996).

Patel et al., "The Role of Proteases During Apoptosis," *FASEB J.* 10:587-597 (1996).

Rothe et al., "The TNFR2-TRAF Signaling Complex Contains Two Novel Proteins Related to Baculoviral Inhibitor of Apoptosis Proteins," *Cell* 83:1243-1252 (1995).

Roy et al., "The c-IAP-1 and c-IAP-2 proteins are direct inhibitors of specific caspases," *The EMBO Journal* 16:6914-6925 (1997).

Roy et al., "The Gene for neuronal Apoptosis Inhibitory Protein is Partially Deleted in Individuals with Spinal Muscular Atrophy," *Cell* 80:167-178 (1995).

Srinivasula et al., "Molecular ordering of the Fas-apoptotic pathway: The Fas/APO-1 protease Mch5 is a CrmA-inhibitable protease that activates multiple Ced-3/ICE-like cysteine proteases," *Proc. Natl. Acad. Sci. USA* 93:14486-14491 (1996).

Takahashi et al. "A single BIR domain of XIAP sufficient for inhibiting caspases," *J. Biol. Chem.* 273 (14): 7787-7790 (1998).

Tian et al., "The expression of native and cultured RPE grown on different matrices," *Physiol. Genomics* 17:170-182 (2004).

Uren et al., "Cloning and Expression of Apoptosis Inhibitory Protein Homologs That Function to Inhibit Apoptosis and/or Bind Tumor Necrosis Factor Receptor-Associated Factors," *Proc. Natl. Acad. Sci. USA*, 93:4974-4978 (1996).

Van Dyke et al., "Monosomy 21 in hematologic diseases," *Cancer Genetics and Cytogenics* 241:137-141 (2003).

Verma and Somia, "Gene therapy—promises, problems and prospects," *Nature* 389:239-242 (1997).

Villa et al., "Caspases and caspase inhibitors", *Trends Biochem Sci*. 22:388-393 (1997).

Weil et al., "Constitutive Expression of the Machinery for Programmed Cell Death," *J. Cell Biol.* 133:1053-1059 (1996).

Xu et al., "Decreased Induction of Fas and FasL in CD4+ T Cells of Mice Deficient in Interferon Regulatory Factor (IRF)-1", *FASEB J*.15(4):A313 (2001).

Yang et al., "Prevention of Apoptosis by Bcl-2: Release of Cytochrome c from Mitochondria Blocked," *Science* 275:1129-1132 (1997).

Zaslav et al., "Significance of a prenatally diagnosed del(10)(q23)," *Am. J. Med. Genet*. 107:174-176 (2002).

Zou et al., "Apaf-1, a Human Protein Homologous to *C. elegans* CED-4, Participates in Cytochrome c-Dependent Activation of Caspase-3," *Cell*, 90:405-413 (1997).

* cited by examiner

SCREENING ASSAYS FOR AGENTS THAT ALTER INHIBITOR OF APOPTOSIS (IAP) PROTEIN REGULATION OF CASPASE ACTIVITY

RELATED APPLICATIONS

This application is a continuation of application Ser. No. 09/799,994, filed Mar. 5, 2001, now U.S. Pat. No. 7,192,728, which is a divisional of application Ser. No. 09/058,969, filed Apr. 10, 1998, now U.S. Pat. No. 6,228,603, which claims the benefit of U.S. Provisional Application No. 60/086,229, filed May 22, 1997, now abandoned, which was converted from application Ser. No. 08/862,087, each of which the entire contents of which is incorporated herein by reference.

ACKNOWLEDGMENT

This invention was made with government support under CA 69381, AG 15402, HL 51399 and AG 14357 awarded by the National Institutes of Health and BC 960435 awarded by the Department of Defense. The government has certain rights in the invention.

BACKGROUND OF THE INVENTION

1. Field of the Invention

The present invention relates generally to molecular medicine and drug screening assays and more specifically to interactions involved in regulating programmed cell death and methods of identifying drugs that alter such interactions.

2. Background Information

Normal tissues in the body are formed either by cells that have reached a terminally differentiated state and no longer divide or by cells that die after a period of time and are replaced from a pool of dividing cells. For example, nervous tissue is formed early in development and the cells of the nervous system reach a terminally differentiated state soon after birth. In general, when nervous tissue is damaged, the nerve cells are incapable of dividing and, therefore, the loss of function due to the damaged nerve cells is not repaired.

In comparison to the nervous system, the skin is composed of stratified layers of epithelial cells, in which the upper (outer) layer of cells constantly is sloughed off and the lower layer of cells divides so as to replace the lost cells. Thus, the skin is an example of a tissue that is maintained in a steady-state, where the number of cells that are lost is equivalent to the number of new cells produced.

In some tissues such as skin, the steady-state is maintained, in part, due to a process of programmed cell death, in which the cells are genetically "programmed" to die after a certain period of time. A cell experiencing programmed cell death undergoes morphologic changes characteristic of apoptosis, including, for example, fragmentation of its DNA and collapse of its nucleus.

Apoptosis is particularly prominent during the development of an organism, where cells that perform transitory functions are programmed to die after their function no longer is required. In addition, apoptosis can occur in cells that have undergone major genetic alterations, thus providing the organism with a means to rid itself of defective and potentially cancer forming cells. Apoptosis also can be induced due to exposure of an organism to various external stimuli, including, for example, bacterial toxins, ethanol and ultraviolet radiation. Chemotherapeutic agents for treating cancer also are potent inducers of apoptosis.

In tissues such as skin and intestine, which are turned-over continually during the life of an organism, the cells forming these tissues undergo programmed cell death throughout the life of the organism. Normally, this process is tightly regulated and the number of cells produced due to cell division is balanced by the number of cells undergoing programmed cell death. However, the regulation of programmed cell death is a complex process involving numerous pathways and, on occasion, defects occur in the regulation of programmed cell death. Given the critical role of this process in maintaining a steady-state number of cells in a tissue or in maintaining the appropriate cells during development of an organism, defects in programmed cell death often are associated with pathologic conditions.

Various disease states occur due to aberrant regulation of programmed cell death in an organism. For example, defects that result in a decreased level of apoptosis in a tissue as compared to the normal level required to maintain the steady-state of the tissue can result in an increased number of cells in the tissue. Such a mechanism of increasing cell numbers has been identified in various cancers, where the formation of a tumor occurs not because the cancer cells necessarily are dividing more rapidly than their normal counterparts, but because the cells are not dying at their normal rate. The first gene identified as being involved in a cell death pathway, the bcl-2 gene, was identified in cancer cells and was shown to function by decreasing the likelihood that cells expressing the gene would undergo apoptosis.

In comparison to cancer, where the likelihood of a cell undergoing apoptosis is decreased, various pathologies are associated with tissues containing cells undergoing a higher than normal amount of apoptosis. For example, increased levels of apoptosis are observed in various neuropathologies, including Parkinson's disease, Alzheimer's disease, Huntington's disease and the encephalopathy associated with acquired immunodeficiency disease (AIDS). Since nerve cells generally do not divide in adults and, therefore, new cells are not available to replace the dying cells, the nerve cell death occurring in such diseases results in the progressively deteriorating condition of patients suffering from the disease.

Numerous genes involved in programmed cell death pathways have been identified and a role for the products of many of these genes has been described. As a result, the cellular pathways leading to apoptosis are being defined. The delineation of programmed cell death pathways provides targets for the development of therapeutic agents that can be used to manipulate the transfer of an apoptotic signal along the pathway. Such agents, for example, can be directed to a step downstream of a defect in a cell death pathway, thus bypassing the defect and allowing a population of cells having the defect to undergo a normal level of apoptosis. Unfortunately, critical steps in cell death pathways remain to be identified. Thus, a need exists to identify the factors involved in programmed cell death pathways. The present invention satisfies this need and provides additional advantages.

SUMMARY OF THE INVENTION

The present invention relates to the regulation of members of the caspase family of cell death proteases by inhibitor of apoptosis (IAP) proteins. For example, the invention relates to the inhibition of caspase-3, caspase-7 or caspase-9 activity by the X chromosome linked inhibitor of apoptosis (XIAP) and to the regulation of pro-caspase activation by an IAP. As disclosed herein, an IAP such as XIAP or a human IAP family protease such as c-IAP-1 or c-IAP-2 can inhibit the activity of a caspase and can prevent the proteolytic processing of a pro-caspase precursor polypeptide, thus preventing formation of the active caspase. In addition, an IAP can bind to an active caspase.

The invention further provides screening assays for identifying agents that modulate the caspase inhibitory activity of an IAP and, therefore, modulate the activity of a caspase or regulate pro-caspase activation by an IAP protein. In addition, the invention provides screening assays for identifying agents that alter the specific association of a caspase and an IAP protein. For example, the invention provides in vitro screening assays for identifying agents that alter the interaction of an IAP protein such as XIAP and a caspase such as caspase-3, caspase-7 or caspase-9. The invention also provides screening assays for identifying agents that alter the specific association of a pro-caspase and an IAP protein. For example, provided are in vitro screening assays for identifying agents that alter the interaction of an IAP protein such as XIAP and a pro-caspase such as pro-caspase-9. The invention further provides screening assays based on cell-free apoptotic systems for identifying agents that alter the caspase inhibitory activity of an IAP and, therefore, regulate the activity of a caspase or the activation of a pro-caspase.

The invention further provides methods of reducing the severity of a pathologic condition in an individual by administering to the individual an agent that alters the caspase inhibitory activity of an IAP and, therefore, alters the level of apoptosis of the cell population. For example, the invention provides methods for reducing the severity of pathologic condition such as a neurodegenerative disease, which is characterized by a pathologically elevated level of apoptosis. In addition, the invention provides methods for reducing the severity of the pathologic condition such as cancer, which is characterized by the pathologic expansion of a population of cells.

DETAILED DESCRIPTION OF THE INVENTION

Figure 1:
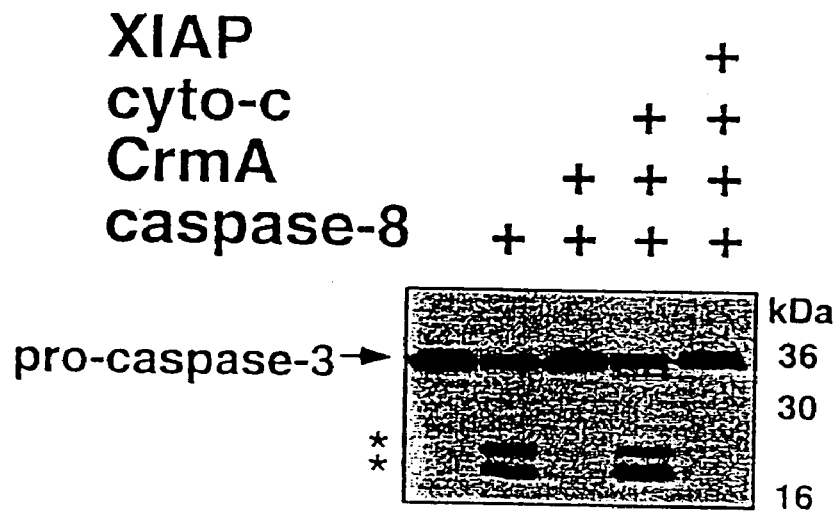
FIG. 1 shows CrmA and XIAP inhibition of caspase-8 and cytochrome c-induced processing and activation of pro-caspase-3 in cytosolic extracts. (A) Western analysis of 293 cell cytoplasmic extracts treated with the indicated agents using antisera specific for the zymogen and large subunit of caspase-3. Molecular weight standards are depicted to the right of panel A. (B) Relative DEVD-AFC cleavage activity of the 293 cell cytoplasmic extracts analyzed in panel A. Data represent the mean+/−SE (n=2).
Figure 1:
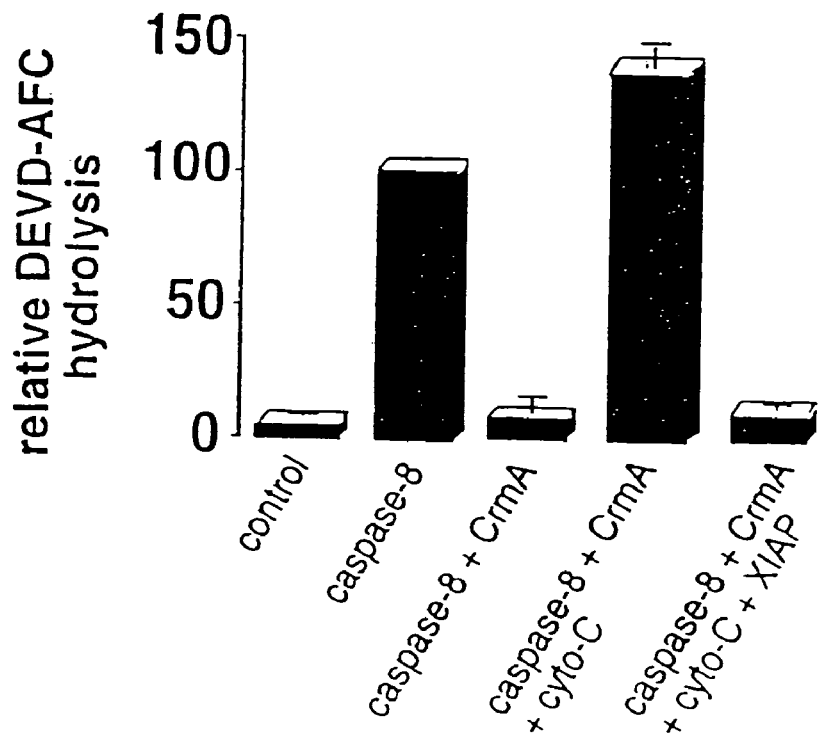

The present invention relates to the regulation of members of the caspase family of cell death proteases by an inhibitor of apoptosis (IAP) protein. For example, the invention relates to the caspase inhibitory activity of an IAP and to the inhibition of the activity of a caspase such as caspase-3, caspase-7 or caspase-9 by eukaryotic IAP (eIAP) proteins such as the X chromosome linked inhibitor of apoptosis (XIAP; Genbank accession number U32974, which is incorporated herein by reference), the cellular IAP proteins (c-IAP-1/HIAP-2/hMIHB and c-IAP-2/HIAP-1/hMIHC; Liston et al., Nature 379:349-353 (1996); Rothe et al., Cell 83:1243-1252 (1995), each of which is incorporated herein by reference); the neuronal apoptosis inhibitory protein (NAIP; Roy et al., Cell 80:167-178 (1995), which is incorporated herein by reference); and survivin (Ambrosini et al., Nature Med. 3:917-921 (1997), which is incorporated herein by reference).

The caspases are a family of cysteine proteases that cleave C-terminal to an aspartic acid residue in a polypeptide and are involved in cell death pathways leading to apoptosis (see Martin and Green, Cell 82:349-352 (1995)). The caspases previously were referred to as the "Ice" proteases, based on their homology to the first identified member of the family, the interleukin-1β (IL-1β) converting enzyme (Ice), which converts the inactive 33 kiloDalton (kDa) form of IL-1β to the active 17.5 kDa form. The Ice protease was found to be homologous to the Caenorhabditis elegans ced-3 gene, which is involved in apoptosis during C. elegans development, and transfection experiments showed that expression of Ice in fibroblasts induced apoptosis in the cells (see Martin and Green, supra, 1995).

Additional polypeptides sharing homology with Ice and ced-3 have been identified and are referred to as caspases, each caspase being distinguished by a number. For example, the originally identified Ice protease now is referred to as caspase-1, the protease referred to as caspase-3 previously was known variously as CPP32, YAMA and apopain, and the protease now designated caspase-9 previously was known as Mch6 or ICE-LAP6. The caspase family of proteases are characterized in that each is a cysteine protease that cleaves C-terminal to an aspartic acid residue and each has a conserved active site cysteine comprising generally the amino acid sequence QACXG (SEQ ID NO: 1), where X can be any amino acid and often is arginine. The caspases are further subcategorized into those that have DEVD (SEQ ID NO: 2) cleaving activity, including caspase-3 and caspase-7, and those that have YVAD (SEQ ID NO: 3) cleaving activity, including caspase-1 (Martin and Green, supra, 1995).

A role for the caspases in apoptosis has been demonstrated by showing that overexpression of each of the identified caspases in various cell types results in apoptosis of the cell. In addition, expression in cells of CrmA, which is expressed by cowpox virus, was shown to protect the cells from undergoing cell death in response to various inducers of apoptosis by inhibiting caspase-1 activity. CrmA also was shown to bind caspase-3 and to inhibit proteolysis of the poly (ADP-ribose) polymerase (PARP) due to caspase-3, whereas a CrmA point mutant lacking the ability to bind caspase-3 did not inhibit proteolysis. PARP, as well as other cellular proteins including lamin B, topoisomerase I and β-actin, are degraded during apoptosis of a cell (see Martin and Green, supra, 1995).

Knock-out studies of various caspase genes indicate that the effects of the caspases may be cell-type specific, although more than one caspase may be expressed in a particular cell type, thereby providing a level of redundancy. For example, mice having the Ice genes knocked-out undergo normal development, indicating Ice activity is not critical for development. Thymocytes from such mice are sensitive to apoptosis induced by dexamethasone or ionizing radiation; however, the thymocytes are resistant to Fas induced cell death (Kuida et al., Science 267:2000-2003 (1995)). In comparison, mice having the caspase-3 genes knocked-out show normal apoptosis in thymocytes, but apoptosis is abnormal in brain cells. The caspase-3 knock-out mice, however, were born at a lower frequency than expected, were smaller than their normal litter mates and died at 1 to 3 weeks (Kuida et al., Nature 384:368-372 (1996)).

Involvement of the caspase proteases in apoptosis can explain, in part, the characteristic changes associated with apoptosis of a cell. For example, caspase induced proteolysis of lamin B, which is involved in attachment of chromatin to the nuclear envelope, can be responsible for collapse of the chromatin associated with apoptosis (Martin and Green, supra, 1995). Caspase induced proteolysis of the 45 kDa subunit of DNA fragmentation factor (DFF-45) activates a pathway leading to fragmentation of genomic DNA into nucleosomal fragments (Liu et al., Cell 89:175-184 (1997)). In addition, caspase induced proteolysis of PARP can prevent the ability of PARP to repair DNA damage, further contributing to the morphologic changes associated with apoptosis. Furthermore, the general expression of such proteins as lamin B and PARP in most cell types can explain the similar appearance of apoptosis observed for various cell types. Other caspase target proteins include sterol regulatory element binding proteins; retinoblastoma (RB) protein; DNA-dependent kinase; U1 70-K kinase; and the large subunit of the DNA replication complex (Wang et al., EMBO J. 15:1012-1020 (1996); Takahashi et al., Proc. Natl. Acad. Sci., USA 93:8395-8400 (1996); Casciola-Rosen et al., J. Exp. Med. 183:1957-1964 (1996); and Ubeda and Habener, J. Biol. Chem. 272:19562-19568 (1997)).

The caspases are present in cells as precursor polypeptides ("pro-caspases"), which lack caspase activity; caspase activation occurs due to proteolytic processing of the pro-caspase. For example, caspase-3 is a heterotetramer composed of approximately 17-20 kDa and 11 kDa polypeptides that are formed by proteolysis of a 32 kDa polypeptide precursor, pro-caspase-3. Cleavage of the pro-caspase-3 proceeds in two steps. The first cleavage results in production of a partially processed large subunit (22-24 kDa) that still contains the pro-domain, and a smaller, fully processed, subunit of about 11 kDa. In the second step, the pro-domain is cleaved from the partially processed large subunit, probably by an autocatalytic process, to produce the 17-20 kDa mature, fully processed large subunit of the active caspase-3 enzyme. Removal of the pro-domain, however, is not necessary for protease activation, as the partially processed caspase also has caspase activity.

In mammalian cells, activation of caspases is achieved through at least two independent mechanisms, which are initiated by distinct caspases but result in activation of common "executioner" caspases. Apoptosis initiated by ligand binding to the Fas receptor is one well described cell death pathway. In this pathway, binding of a ligand to Fas allows the intracellular domain of Fas to bind the intracellular MORT1 (FADD) protein, which, in turn, binds to caspase-8 (MACH; FLICE; Mch5; see Boldin et al., *Cell* 85:803-815 (1996); Muzio et al., *Cell* 85:817-827 (1996)). These results define caspase-8 as the most upstream caspase involved in the Fas cell death pathway. In addition, caspase-3 is activated in the Fas cell death pathway, suggesting that an upstream protease such as caspase-8 or a protease activated by caspase-8 is involved in caspase-3 activation.

Caspase activation also can involve cytochrome c, which in mammalian cells is often released from mitochondria into the cytosol during apoptosis (Liu et al., *Cell* 86:147-157 (1996); Kharbanda et al., *Proc. Natl. Acad. Sci., USA* 94:6939-6942 (1997); Kluck et al., *Science* 275:1132-1136 (1997); and Yang et al., *Science* 275:1129-1132 (1997), each of which is incorporated herein by reference). Upon entering the cytosol, cytochrome c induces the ATP- or dATP-dependent formation of a complex of proteins that results in proteolytic activation of pro-caspase-3 and apoptotic destruction of nuclei (Liu et al., supra, 1996). Among the members of this complex are the CED-4 homolog Apaf-1, and caspase-9 (Apaf-3; Liu et al., supra, 1996; Li et al., *Cell* 91:479-489 (1997); Zou et al., *Cell* 90:405-413 (1997)). XIAP, c-IAP-1 and c-IAP-2 suppress apoptosis induced by stimuli known to cause release of cytochrome c from mitochondria and can inhibit caspase activation induced by cytochrome c in vitro. Yet, to date, the mechanism through which XIAP and other IAP family proteins block cytochrome c-induced apoptosis is not known.

As disclosed herein, XIAP, cIAP-1 and cIAP-2 block two distinct pathways of caspase activation by inhibiting different caspases. Caspase-8-induced protease activation was suppressed by XIAP, cIAP-1 and cIAP-2 at the level of caspase-3, by inhibiting active caspase-3 following its initial cleavage to p24 and p12 subunits (see Example V). The p24 subunit, as discussed-above, is a partially processed form of caspase-3, which results from an initial cleavage of pro-caspase-3 but which has not been processed further by removal of its N-terminal pro-domain. Furthermore, in a cell-free system activated by addition of exogenous active caspase-8 and incubated with GST-XIAP, glutathione-Sepharose pulls down the p24 form of the large subunit of caspase 3 with GST-XIAP (Example V; FIG. 2A). In cells overexpressing Fas (CD95), a known activator of caspase-8, XIAP complexed with the p24 form of partially processed caspase-3, and inhibited Fas-mediated apoptosis (Example V; FIG. 2B). In summary, these results indicate that XIAP inhibits the caspase-8 apoptotic pathway at the level of caspase-3, allowing caspase-8 to induce processing of caspase-3 but preventing subsequent autocatalytic maturation by directly binding to and inhibiting the partially processed caspase-3 enzyme.

Through a distinct mechanism, XIAP, c-IAP-1 and c-IAP-2 also inhibit the apoptotic pathway induced by cytochrome c. In contrast to the results seen in caspase-8 treated extracts, where pro-caspase-3 was processed to large and small subunits, addition of XIAP to cytochrome c treated extracts inhibited processing of pro-caspase-3 and also pro-caspases-6 and -7 (Example V; FIG. 2A). Moreover, isolation of GST-XIAP protein from cytochrome c-treated extracts using glutathione-Sepharose revealed no associated caspase-3 molecules. These results indicate that XIAP inhibits the cytochrome c pathway upstream of caspases-3, -6 and -7, since little or no processing of these caspases occurs in the presence of XIAP.

Figure 3:
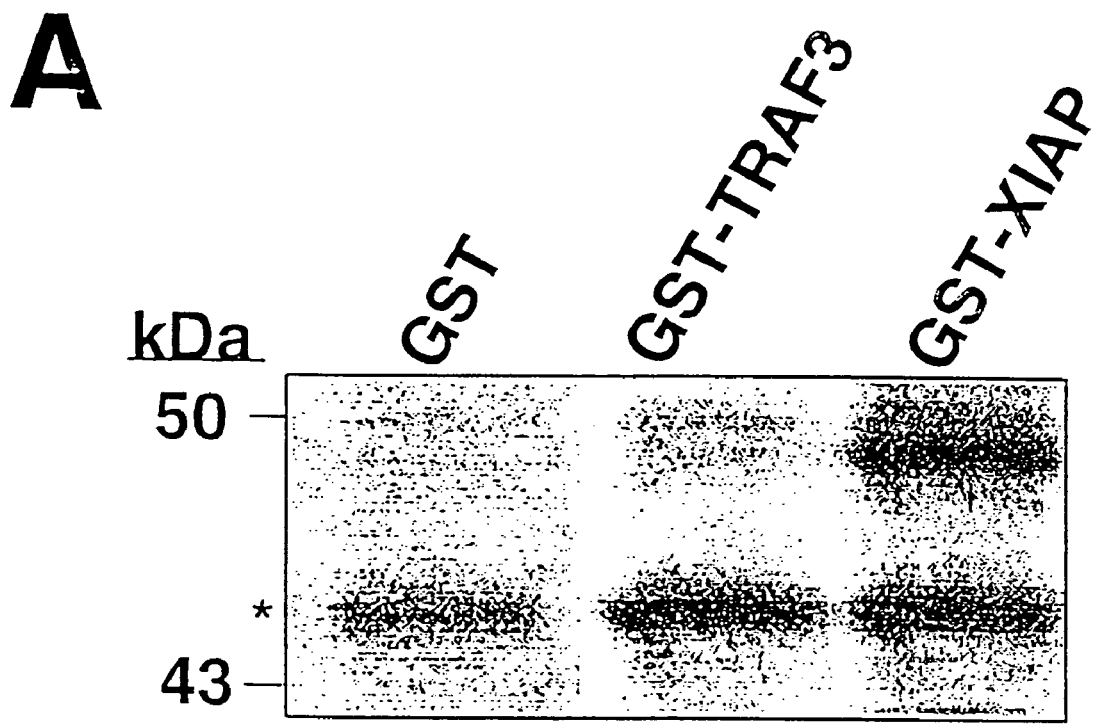
FIG. 3 shows binding of pro-caspase-9 to XIAP, c-IAP-1 and c-IAP-2. (A) SDS-PAGE and autoradiographic analysis of $^{35}$S-L-methionine labeled U937 cell lysates incubated with GST, GST-TRAF-3 (1-357) or GST-XIAP. The asterisk indicates a background band which was non-specifically recovered with the beads and serves as a loading control. (B) SDS-PAGE and autoradiographic analysis of reticulocyte lysates containing in vitro translated $^{35}$S-labeled pro-caspase-9 with GST-XIAP, c-IAP-1, c-IAP-2 or a GST-control fusion protein immobilized on glutathione-Sepharose. As a control, 1.5 µl of the in vitro translated reaction (IVT) is included in the far right lane.
Figure 3:
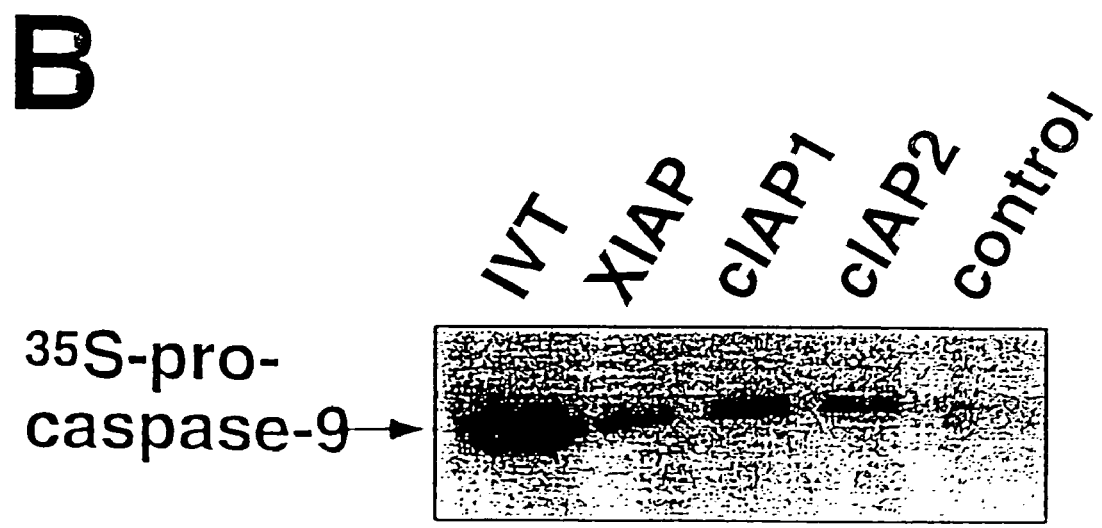
Figure 4:
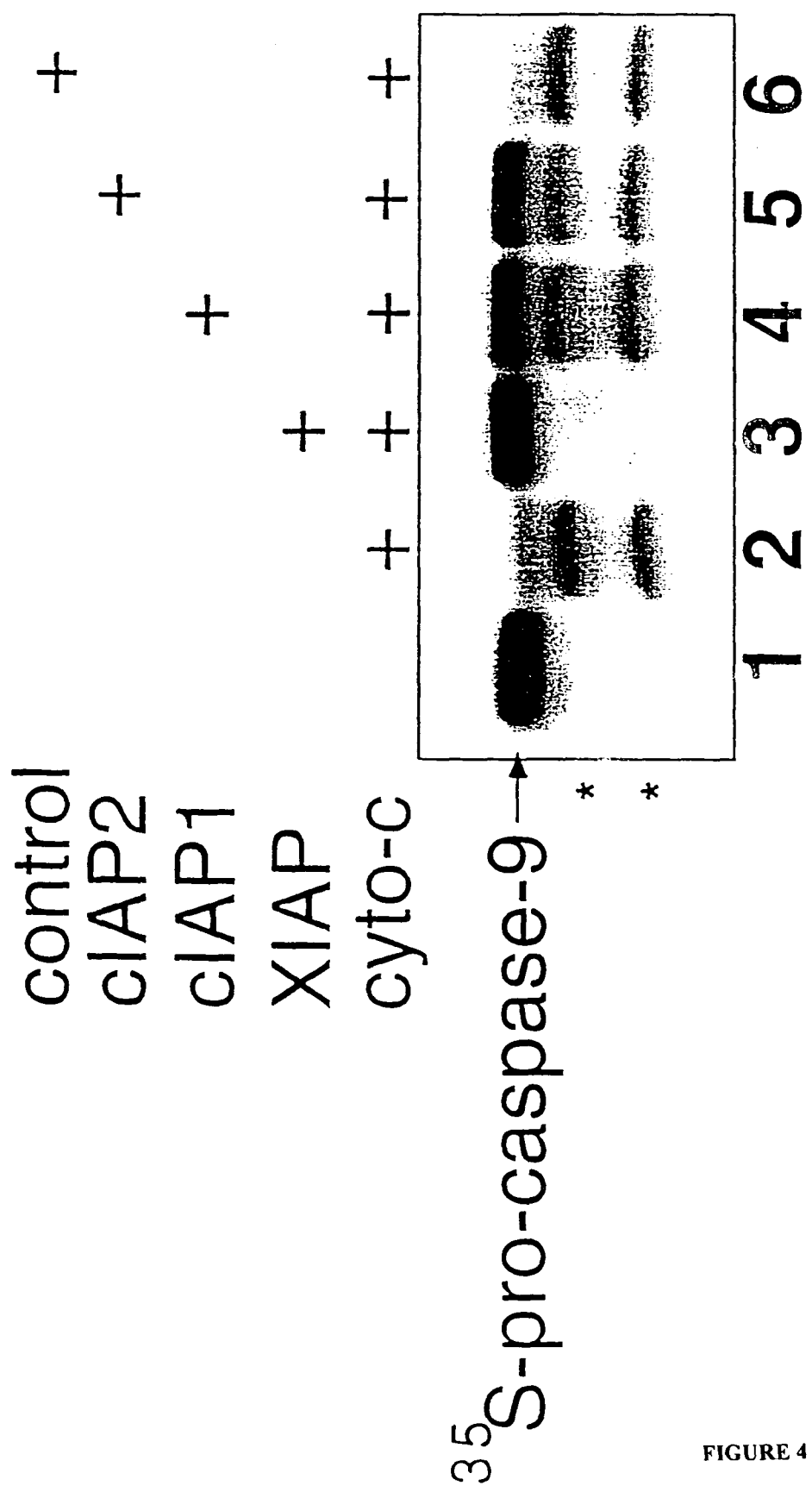
FIG. 4 shows inhibition of cytochrome c-induced caspase-9 processing by XIAP, c-IAP-1, and c-IAP-2. Shown is SDS-PAGE and autoradiographic analysis of in vitro translated $^{35}$S-labeled pro-caspase-9 added to 293 cell cytosolic extracts which were then incubated with cytochrome c and dATP (lanes 2-6) or without cytochrome c and dATP (lane 1) in the presence or absence of the indicated GST-IAP or control GST protein. The positions of the processed subunits of caspase-9 are indicated by asterisks.
Figure 5:
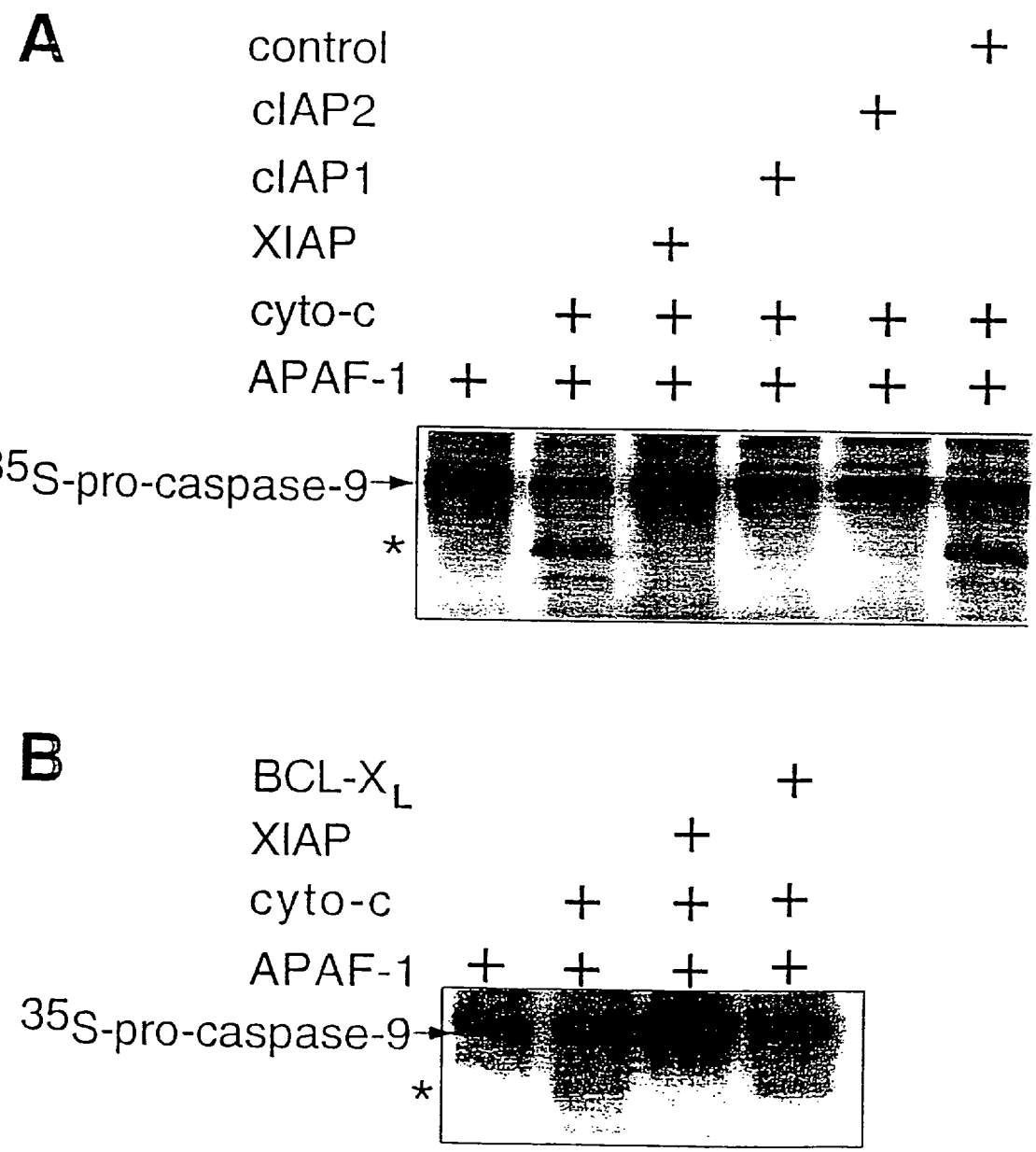
FIG. 5 shows that pro-caspase-9 processing requires Apaf-1 and cytochrome-c and is inhibited by XIAP, c-IAP-1 and c-IAP-2. In vitro translated $^{35}$S-labeled pro-caspase-9 and Apaf-1 were incubated individually or together with cytochrome c and dATP. (A) Processing of pro-caspase-9 in the absence or presence of GST-IAPs monitored by SDS-PAGE and autoradiography. (B) Processing of pro-caspase-9 in the absence or presence of Bcl-$X_L$ monitored by SDS-PAGE and autoradiography. An asterisk indicates the position of the processed large subunit of caspase-9.
Figure 6:
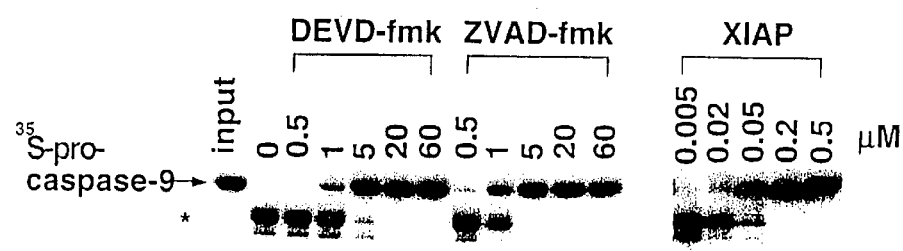
FIG. 6 shows a comparison of pro-caspase-9 inhibition by Ac-DEVD-fmk, zVAD-fmk and XIAP. Shown is SDS-PAGE and autoradiographic analysis of in vitro translated $^{35}$S-labeled pro-caspase-9 added to cytosolic extracts from 293 cells treated with cytochrome c and dATP, which were incubated in the presence of the indicated concentrations of inhibitors. The asterisk denotes the processed large subunit of caspase-9.

As further disclosed herein, a 50 kDa protein associates specifically with GST-XIAP, as indicated by the recovery of a protein of this size using glutathione-Sepharose (Example VI; FIG. 3A). Caspase-9 is known to have a molecular mass of about 50 kDa. As disclosed in Example VI, GST-XIAP, GST-c-IAP-1 and GST-c-IAP-2, but not GST control proteins, associated with in vitro translated pro-caspase-9 (FIG. 3B); these IAP family proteins also bind to pro-caspase-9 in vivo (Example X; FIG. 8D). Furthermore, c-IAP-1 and c-IAP-2 inhibit proteolytic processing of pro-caspase-9 induced by cytochrome c in cytosolic extracts and in an in vitro reconstituted system containing cytochrome c and dATP, Apaf-1 and pro-caspase-9 (Examples VII and VIII; FIGS. 4 and 5). In cytosolic extracts, XIAP was a more potent inhibitor of cytochrome c-mediated processing of pro-caspase-9 than either Ac-DEVD-Fmk or zVAD-fmk, two well-characterized caspase inhibitors (Example IX; FIG. 6). These results indicate that XIAP, c-IAP-1 and c-IAP-2 can associate with the zymogen of caspase-9 and block its processing. Coupled with data described hereinabove, these results indicate that IAP-mediated inhibition of cytochrome c induced activation occurs upstream of caspase-3, at least in part through direct inhibition of pro-caspase-9 processing.

As further disclosed herein, XIAP, cIAP-1, and cIAP-2 directly inhibit active caspase-9. In one assay, recombinant pro-caspase-3 was used to monitor activity of caspase-9. Whereas incubation of recombinant active caspase-9 with purified recombinant pro-caspase-3 resulted in proteolytic processing of pro-caspase-3 as determined by immunoblot analysis, addition of an equimolar concentration of XIAP relative to caspase-9 strongly inhibited cleavage of pro-caspase-3 (Example IX; FIG. 7A). These results were corroborated by measuring caspase-9 activity through release of AFC fluorophore from the DEVD-AFC substrate: the results demonstrate that XIAP, c-IAP-1 and cIAP-2 each efficiently inhibit pro-caspase-3 activation and cleavage of the tetrapeptide substrate whereas various GST control proteins had no significant effect (see FIG. 7B).

Given the inhibitory effect of XIAP, c-IAP-1 and c-IAP-2 on pro-caspase-9 activation in vitro, these IAP family proteins were assayed for the ability to protect against caspase-9-induced apoptosis in intact cells and to inhibit downstream events, such as processing of pro-caspase-3. 293T cells were transfected with epitope-tagged FLAG-caspase-9 alone or in combination with myc-tagged IAP family proteins. Caspase-9-induced proteolytic cleavage of pro-caspase-3 and Ac-DEVD-AFC cleavage activity was markedly reduced in 293T cells co-transfected with FLAG-caspase-9 and XIAP, c-IAP-1 or c-IAP-2, as compared to 293T cells transfected with FLAG-caspase-9 alone (Example X; FIG. 8B). The observed inhibition of pro-caspase-3 processing by XIAP, c-IAP-1 or c-IAP-2 was accompanied by a reduction in the number of apoptotic 293T cells (Example X; FIG. 8C). Thus, IAP family proteins inhibit active caspase-9 in vitro and in vivo, and inhibition of active caspase-9 can be a mechanism through which the IAP family proteins inhibit cytochrome c-induced apoptosis.

As described above, XIAP, c-IAP-1 and c-IAP-2 arrest proteolytic processing of the pro-caspase-3 precursor polypeptide to active caspase-3 and result in accumulation of the 22-24 kDa intermediate proteolytic product of caspase-3 comprising the large subunit and pro-domain. These IAP proteins also bind to caspase-3 and caspase-7, as well as to the 22-24 kDa caspase-3 large subunit and pro-domain, but do not bind to the unprocessed pro-caspase-3 or pro-caspase-7 precursor polypeptides (Example II). These IAP proteins prevent the completion of caspase-3 processing by binding to the partially processed protease and preventing the autocatalytic removal of the pro-domain by caspase-3. In addition, XIAP prevents apoptotic-like destruction of nuclei in a cell-free apoptotic system (Example I.B.1) and prevents Bax-induced apoptosis of transfected mammalian cells, both in association with inhibition of caspase-3 and caspase-3-related proteases (Example III). Accordingly, the present invention is based on the discovery that IAP proteins can modulate apoptosis by directly binding to caspases and inhibiting their activity, and, as described above, that IAP proteins also can modulate apoptosis by binding to and inhibiting a pro-caspase such as pro-caspase-9.

IAP proteins initially were identified in baculovirus cells as proteins that inhibited apoptosis of insect cells infected with the virus (Crook et al., *J. Virol.* 67:2168-2174 (1993); Birnbaum et al., *J. Virol.* 68:2521-2528 (1994), each of which is incorporated herein by reference). Examination of the viral IAP polypeptides revealed a conserved sequence comprising two repeated cysteine-histidine containing regions, designated the baculovirus IAP repeat ("BIR"), at the N-terminal and central portion of the polypeptide and a RING finger domain in the C-terminal portion (Birnbaum et al., supra, 1993). Expression of the baculovirus IAP protein in mammalian cells also prevents apoptosis of the cells due to gene transfer-mediated overexpression of an exogenous Ice protease (caspase-1), indicating that IAP's are evolutionarily conserved (Duckett et al., *EMBO J.* 15:2685-2694 (1996), which is incorporated herein by reference). Homologs of the baculovirus IAP proteins subsequently were identified in humans and in *Drosophila* (Hay et al., *Cell* 83:1253-1262 (1995), which is incorporated herein by reference; see, also, Rothe et al., supra, 1995; Duckett et al., supra, 1996; Roy et al., supra, 1995; Liston et al., supra, 1996; Uren et al., *Proc. Natl. Acad. Sci., USA* 93:4974-4978 (1996); Ambrosini et al., supra, 1997). However, prior to the present disclosure, the means by which an IAP protein modulates apoptosis was not known.

As disclosed herein, IAP proteins have a caspase inhibitory activity. Specifically, eIAP proteins such as XIAP, c-IAP-1 and c-IAP-2 reduce or prevent apoptosis by inhibiting activation of pro-caspases and by inhibiting caspase activity. As used herein, reference to an IAP protein as an "inhibitor of caspase activation" or "inhibitor of caspase activity" or as having "caspase inhibitory activity" means that the proteolytic activity of a caspase in the presence of the IAP or when bound to the IAP is less than it would be in the absence of the IAP or in the absence of IAP binding. This caspase inhibitory activity of an IAP can be due to a) inhibition of an upstream caspase required for proteolytic activation of a downstream caspase; b) inhibition of the completion of caspase processing by the IAP; or c) a direct inhibitory effect of the IAP on caspase proteolytic activity.

In all three cases above, the caspase inhibitory activity of an IAP is identifiable, for example, by a lower level of hydrolysis of a specific substrate by the caspase in the presence of the IAP as compared to the activity in the absence of the IAP. For example, addition of XIAP, c-IAP-1 or c-IAP-2 to a cell-free extract, which otherwise would exhibit caspase-3 mediated proteolysis of a peptide substrate, substantially reduced the amount of proteolysis of the peptide (see Examples I.B.3 and IV). In addition, expression of a recombinant XIAP in a cell prevented apoptosis of the cells that otherwise would undergo apoptosis due to caspase activation (see Examples III and V). In view of the specificity of binding of an IAP to a caspase, such as the binding of XIAP, c-IAP-1 or c-IAP-2 to caspase-3 or caspase-7, or the binding of an IAP to a pro-caspase such as the binding of XIAP, c-IAP-1 and c-IAP-2 to pro-caspase-9, and the role of caspase activation in apoptosis, it should be recognized that caspase activity can be identified directly, for example, by examining proteolysis (hydrolysis) of a specific substrate, or indirectly, for example, by identifying morphological changes in a cell or a cell nucleus characteristic of apoptosis, which is dependent on those caspases that the IAP inhibits, or using an antibody that binds to the active caspase, but not to the inactive caspase, or that binds to a proteolytic product of the substrate.

At least ten caspases have been identified in mammalian cells, and homologs of these caspases are expressed in other eukaryotic organisms. In addition, numerous IAP proteins are known, including viral and eukaryotic IAP's. However, while apoptosis appears to uniformly require the participation of caspases (Weil et al., *J. Cell Biol.* 133:1053-1059 (1996)), the particular caspases required vary depending on the cell-type and the stimulus used to trigger cell death (Kuida et al., supra, 1995, 1996). Thus, the ability of each IAP family member to inhibit apoptosis can vary depending on the cell and the stimulus involved and, therefore, the particular caspases activated.

As disclosed herein, for example, the caspase inhibitory activity of XIAP, c-IAP-1 and c-IAP-2 was specific for caspase-3 and caspase-7, whereas XIAP had little or no direct inhibitory effect on caspase-1, caspase-6 or caspase-8 activation. Furthermore, the inhibitory effect due to the IAP proteins localizes with the three BIR domains present within amino acid positions 1 to 336 of XIAP, positions 1 to 350 of c-IAP-1, and positions 1 to 335 of c-IAP-2. Thus, for example, addition of a glutathione S-transferase-BIR (GST-BIR) fusion protein to an in vitro assay inhibited caspase-3 and caspase-7 hydrolysis of a peptide in vitro (Examples II and IV), and expression of a BIR construct in a cell prevented Bax-induced cell death (Example III).

The results disclosed herein indicate that the ability of an IAP protein to bind to a caspase correlates with the ability of the IAP to inhibit the proteolytic activity of that caspase and, therefore, to inhibit apoptosis. In view of the present disclosure, it will be recognized that the regulation of caspase activation by IAP proteins likely is a general phenomenon. Accordingly, the present invention provides the broader disclosure that IAP proteins regulate caspase activation in a cell and, therefore, are involved in regulating apoptosis, and further provides methods for identifying which IAP proteins regulate which caspases. For example, as disclosed herein, the human XIAP protein and the IAP family proteins, c-IAP-1 and c-IAP-2, inhibit caspase-3 and caspase-7 activity (Example IV). Furthermore, the human XIAP, c-IAP-1 and c-IAP-2 proteins also inhibit caspase-9 activity (Examples IX and X).

Using the disclosed methods for determining that XIAP regulates caspase-3, -6 and -7 activation by inhibiting the upstream protease caspase-9 in, and that XIAP directly binds to and inhibits the activity of caspase-3 and caspase-7 as well as caspase-9, the particular IAP proteins that regulate the activation of other caspases can be identified. Example VI discloses the identification of caspase-9 as the upstream protease inhibited by XIAP in the cytochrome c pathway using GST-XIAP and metabolically labeled extracts. Cell-free assays can be particularly useful for examining the ability of the various known IAP proteins to regulate the activity of various known caspases by identifying changes in the hydrolysis of a specific substrate (Example I.B.3 and Example V). The cell-free system-utilizes a cytosolic extract obtained from a cell, particularly a mammalian cell or other eukaryotic cell. Upon the addition of cytochrome c and dATP to the cytosolic extract, an apoptotic program, including proteolytic processing and activation of certain caspases and apoptotic-like destruction of exogenously added nuclei is initiated (Liu et al., supra, 1996). This cell-free-system mimics a commonly observed feature of apoptosis in vivo, where release of cytochrome c from mitochondria into the cytosol is associated with the initiation of apoptosis (Kluck et al., supra, 1997; Liu et al., supra, 1996). In addition, an "upstream" caspase such as caspase-8 can be produced recombinantly in an active form and added to cytosolic extracts to initiate the apoptotic program (see Example I.B.3 and Example V).

The cell-free apoptotic system was used to examine the effect of XIAP on the apoptotic process. Purified nuclei remained mostly intact when incubated in control cytosols, whereas addition of cytochrome c and dATP to the cytosols caused apoptotic-like destruction of nearly all nuclei (Example I.B.2). Addition of XIAP simultaneously with cytochrome c and dATP substantially inhibited nuclear destruction, whereas an equivalent amount of added Bcl-2 protein had no protective effect.

In addition to inhibiting apoptosis of nuclei, XIAP, as well as c-IAP-1 and c-IAP-2, also inhibited caspase activation in the cell-free apoptosis system, whereas numerous control proteins had little or no effect. Similar results were obtained using cytosols prepared from 293 kidney cells or from Jurkat T cells, indicating that the results are representative of a general effect. Furthermore, in cytosolic extracts prepared from 293T cells two days after transfection with either pcDNA3-XIAP, which expresses XIAP, or the pcDNA3 control plasmid, caspase-specific substrate hydrolysis was reduced by greater than 50% in extracts prepared from the XIAP expressing cells as compared to control extracts. Thus, exogenously added XIAP, c-IAP-1 and c-IAP-2, and endogenously produced XIAP each inhibit cytochrome c-induced caspase activation in the cell-free apoptotic system. Addition of XIAP to the cell-free apoptotic extracts prior to cytochrome c also prevented proteolytic processing of the pro-caspase-3 precursor polypeptide from its 32 kDa form into the active 17-20 kDa form (Example I.B.3). The prevention of caspase-3 processing in such cytochrome c treated extracts can be due to the inhibition by the IAP of an unidentified upstream caspase, which processes pro-caspase-3, or can reflect inhibition of an auto-amplification process, whereby activation of a small amount of caspase-3 leads to proteolytic processing of more pro-caspase-3 by active caspase-3, and whereby the IAP binding to and inhibition of the active caspase-3 prevents additional processing of pro-caspase-3.

As an alternative to using cytochrome c and dATP to induce the apoptotic program in the cell-free system, recombinant active caspase-8, which associates with Fas and TNF-R1 receptor complexes and functions as an upstream initiator of proteolytic cascades leading to caspase-3 activation and apoptosis, was added to the extracts. Caspase-8 stimulated cleavage of pro-caspase-3, yielding the 17-20 kDa large subunit (active caspase-3) characteristic of protease activation, whereas, in the presence of XIAP, caspase-8 induced the production of a partially processed 22-24 kDa form of caspase-3 (Example I.B.3). Thus, XIAP did not prevent the initial cleavage of caspase-3 that was induced by caspase-8, but inhibited subsequent processing events that produce the mature large subunit. Previous studies have shown that the completion of caspase-3 processing, including removal of the pro-domain, is an autocatalytic event, wherein the partially processed caspase-3 completes its own processing, removing its own pro-domain (Martin et al., EMBO J. 14:5191-5200 (1995), which is incorporated herein by reference).

The specificity of caspase inhibitory activity of XIAP, c-IAP-1 and c-IAP-2 also was examined. Purified XIAP, for example, as a GST fusion protein, inhibited greater than 95% of the substrate proteolysis by caspase-3 and by caspase-7, but did not interfere with substrate cleavage by caspase-1, caspase-6 or caspase-8, even when added at a 50-fold molar excess (Example II). Furthermore, a GST fusion protein containing only the three BIR domains of XIAP (residues 1-337) also potently inhibited caspase-3 and caspase-7, whereas a GST-fusion containing the RING domain (338-497), as well as several control GST-fusion protein, had no significant effect. Similar results were obtained using c-IAP-1 or c-IAP-2, as well as BIR constructs of these IAP proteins. Thus, XIAP, c-IAP-1 and c-IAP-2 specifically inhibit caspase-3 and caspase-7 activity, but have little or no inhibitory effect on caspase-1, caspase-6 or caspase-8.

In addition to inhibiting their proteolytic activity, XIAP, c-IAP-1 and c-IAP-2 specifically associate with purified active caspase-3 and caspase-7 in vitro, as well as to the partially processed 22-24 kDa large subunit and pro-domain, but not to the unprocessed precursor polypeptides of caspase-3 and caspase-7 (Examples I.B.3 and IV). Furthermore, XIAP, c-IAP-1 and c-IAP-2 specifically associate with pro-caspase-9 in vitro (Example VI). Thus, in contrast to the zymogens of caspase-3 and caspase-7, pro-caspase-9 associates specifically with IAP family proteins. These results demonstrate that an in vitro binding assay provides an additional method for identifying the IAP proteins that specifically associate with particular caspases and, therefore, are likely candidates for regulation of the activities of these caspases.

As used herein, the term "specifically associate" or "specifically bind," when used in reference to an IAP protein and a caspase or pro-caspase, means that the IAP and the caspase or pro-caspase have a binding affinity for each other such that they form a bound complex. For example, as disclosed herein, XIAP exhibited tight, reversible binding to caspase-3 ($K_i \approx 0.7$ nM) and to caspase-7 ($K_i \approx 0.2$ nM; see Example II), values that compare favorably with viral inhibitors of caspases, cowpox CrmA ($K_i \approx 0.01$-$0.95$ nM) and baculovirus p35 ($K_i \approx 1.0$ nM), for their target caspases (Zhou et al., J. Biol. Chem. 272:7797-7800 (1997), which is incorporated herein by reference; see, also, Bertin et al., J. Virol. 70:6251-6259 (1996)). In view of the specificity of binding of IAP proteins and caspases or pro-caspases, an in vitro binding assay provides the basis of a screening assay for identifying agents that can alter the specific association of an IAP and a caspase or pro-caspase and, therefore, can be useful to modulate the level of apoptosis in a cell.

Based on transient transfection assays, it is further disclosed that XIAP inhibits processing and activation of caspases in intact cells. Human 293T cells were transfected with a human Bax expression vector. Bax induces mitochondrial permeability transition, which is predicted to cause release of cytochrome c and processing of caspase-3, caspase-6 and caspase-7 (Xiang et al., Proc. Natl. Acad. Sci., USA 93:14559-14563 (1996)).

Bax expression in the transfected cells resulted in a 7- to 10-fold increase in cell death as detected by vital staining and an 8- to 10-fold increase in apoptosis as measured by DNA fragmentation, whereas cotransfection of a plasmid expressing XIAP significantly inhibited Bax-induced apoptosis (Example III). A myc-tagged version of XIAP containing only the BIR domains was as effective as the full length XIAP protein at suppressing Bax-induced cell death and apoptosis, whereas the RING domain of XIAP was inactive. The caspase inhibiting peptide, zVAD-fmk, also inhibited apoptosis in the Bax transfected cells, consistent with a role for caspases in Bax-induced cell death in these cells. Thus, XIAP, particularly a fragment of XIAP comprising the BIR domains, which can bind to active caspase-3 and caspase-7 and inhibit their protease activity, also can suppress Bax-induced apoptosis in intact cells. In addition, these results demonstrate that transfection assays in intact cells can be used to confirm that a particular IAP protein regulates activation of a selected caspase, as initially determined using in vitro assays, and can be useful in screening assays to identify agents that modulate the caspase inhibitory activity of an IAP, particularly when used in combination with a substrate hydrolysis assay or an immunoblot analysis (see Examples I.B.3 and III).

The invention therefore provides screening assays for identifying an agent that modulates the caspase inhibitory activity of an IAP by altering the specific association of a caspase and an inhibitor IAP protein. The method comprises contacting the caspase and the IAP, under conditions that allow the caspase and the IAP to specifically associate, with an agent suspected of being able to alter the association of the caspase and the IAP; and detecting an altered association of the caspase and the IAP, thereby identifying an agent that alters the association of the caspase and the IAP. For example, the invention provides in vitro screening assays for identifying agents that alter the specific binding of an eIAP such as XIAP, c-IAP-1 or c-IAP-2 and a caspase such as caspase-3, caspase-7 or caspase-9. In addition, the invention provides cell based screening assays for identifying agents that alter the caspase inhibitory activity of an IAP by expressing a recombinant IAP protein in the cell and determining the effect of an agent on the level of caspase activity or caspase activation in the cell lysate. A cell based assay can be particularly useful, for example, to confirm that an agent identified using a cell-free system or an in vitro assay also is effective in a cell for altering the association of an IAP and a caspase or for modulating the regulation of activation of a caspase by an IAP and, therefore, for modulating apoptosis.

Screening assays also can be used to identify an agent that alters the specific association of a pro-caspase and an IAP protein. The steps of the method include contacting the pro-caspase and the IAP, under conditions that allow the pro-caspase and the IAP to specifically associate, with an agent suspected of being able to alter the association of the pro-caspase and the IAP; and detecting an altered association of the pro-caspase and the IAP, thereby identifying an agent that alters the association of the pro-caspase and the IAP. Such an assay for identifying an agent that alters the specific association of an IAP and a pro-caspase can be, for example, an in vitro, or cell based assay. In such a method, a particularly useful IAP can be an eIAP, including an X chromosome linked IAP such as XIAP, or an eIAP such as cIAP-1 or c-IAP-2. Based on the results disclosed herein, a particularly useful pro-caspase can be, for example, pro-caspase-9.

As used herein, the term "pro-caspase" refers to the zymogen or inactive precursor form of a caspase. A pro-caspase generally is converted to an active caspase form by limited proteolysis.

As used herein, the term "agent" means a chemical or biological molecule such as a simple or complex organic molecule, a peptide, a peptidomimetic, a protein or an oligonucleotide. Synthetic peptides are agents particularly useful in the methods of the invention. A synthetic peptide can contain, for example, amino acids, amino acid equivalents or other non-amino groups, related organic acids such as p-aminobenzoic acid (PABA) and can include amino acid analogs having substituted or modified side chains or functional groups. The cell-free apoptotic system and in vitro assays disclosed herein (Examples I and II) are particularly useful as drug screening assays in that they can be automated, which allows for high through-put screening of randomly designed agents in order to identify those agents that effectively alter the caspase inhibitory activity of an IAP or alter the specific association of an IAP protein and a caspase or pro-caspase.

As used herein, the term "alter" means that the agent can increase or decrease the relative affinity of a caspase, or pro-caspase, and an IAP protein or can alter the caspase inhibitory activity of an IAP. The ability of an agent to alter the association of an IAP protein and a caspase or pro-caspase, for example, can be identified using in vitro binding assays (see Examples I and II). In particular, the ability of an agent to alter the affinity of binding of an IAP and a caspase or pro-caspase can be identified by determining the dissociation constant of the complex, thus providing a means to select agents that increase or decrease the specific association of an IAP and a caspase or pro-caspase to various extents (Example II). The ability to select agents that variously alter the specific association of a caspase, or pro-caspase, and an IAP provides a means to closely regulate that level of apoptosis of a population of cells, particularly a population of cells involved in a pathologic condition.

An agent that alters the association of an IAP and a caspase or alters the caspase inhibitory activity of an IAP can be useful for altering the level of apoptosis of a population of cells ex vivo, including cells in culture or, in an individual. For example, an agent that alters the caspase inhibitory activity of an IAP can be incubated with cells ex vivo in order to decrease the level of apoptosis in the cells. Such a method can be useful, for example, for culturing cells that otherwise undergo apoptosis when placed in culture or for treating an individual's cells ex vivo, either to examine the effect of such a treatment on the cells as a prelude to treating the individual or where the cells are to be readministered to the individual. Similarly, an agent can be used to treat a mixed population of cells in culture in order to selectively induce apoptosis in one of the populations of cells, thereby allowing selection of the remaining population. Such a method requires that agents that are identified as having the ability to decrease the caspase inhibitory activity of an IAP, be screened further to identify those taken up more selectively by one cell population as compared to the other cell population. Such methods are well within the level of skill in the art. Thus, the invention provides methods of modulating the level of apoptosis of a population of cells in culture by contacting the cells with an agent that alters the caspase inhibitory activity of an IAP in the cells.

The invention further provides a method of reducing the severity of a pathologic condition in an individual by administering to the individual an agent that alters the caspase inhibitory activity of an IAP, thereby altering the level of apoptosis of a cell population. An agent useful for treating a pathologic condition that is characterized, at least in part, by an undesirably high level of expansion of a cell population can reduce or inhibit the ability of IAP to inhibit caspase activation, such that the active caspase can effect its action in a cell death pathway and apoptosis of the cells can occur. For example, a tumor in a cancer patient forms due to expansion of the cancer cell population due either to increased division of the cancer cells or a decreased level of apoptosis, depending on the particular cancer. By inhibiting the ability of an IAP to inhibit caspase activity, the cell death pathway can result in apoptosis of the cancer cells. Similarly, such an agent can be useful for treating an autoimmune disease, where it is desirable to induce apoptosis in the immunoeffector cells that mediate the disease. In addition, undesirable expansion of cell populations occur in conditions such as psoriasis and in restenosis. Thus, the present invention provides methods for treating a disease characterized by a pathologically high level of expansion of a cell population by administering to an individual having the disease an agent that reduces or inhibits the specific association of a caspase and an IAP such that the caspase inhibitory activity of the IAP is reduced or inhibited.

An agent that increases the specific association of a caspase and an IAP or that increases the caspase inhibitory activity of an IAP also can reduce or inhibit the level of apoptosis of a population of cells in an individual. Such an agent is useful, for example, to prevent apoptosis of neuronal cells as occurs in neurodegenerative diseases, including Parkinson's disease, Huntington's disease, Alzheimer's disease and the encephalopathy that occurs in AIDS patients. Thus, the invention provides methods of treating an individual having a disease characterized by a pathologically elevated level of apoptosis of a cell population by administering an agent that increases the specific association of an IAP and a caspase, thereby increasing the caspase inhibitory activity of the IAP and reducing or inhibiting apoptosis of the cell population. Accordingly, an agent that is identified using a method of the invention as having the ability to alter the association of an IAP and a caspase or that can alter the caspase inhibitory activity of an IAP can be useful as a medicament for treating a disease such as cancer or a neurodegenerative disease or other disease characterized, at least in part, by an altered level of apoptosis.

An agent that modulates the regulation of caspase activation by an IAP protein also can be identified, for example, in an in vitro assay by contacting the caspase with an IAP that is known to inhibit the activity of the particular caspase, with an agent suspected of being able to modulate the activity of the caspase and measuring the proteolytic activity of the caspase. For example, an IAP such as XIAP, or fragment of an IAP comprising the BIR domains, can be incubated in vitro with a caspase such as caspase-3, which can be active caspase-3, including either the fully or partially processed caspase-3, and the agent. In addition, since recombinant XIAP can block the activation and processing of certain pro-caspases in cytosolic extracts, XIAP can be incubated with or without an agent in a cytosolic extract containing cytochrome c and dATP. In the absence of an agent that modulates regulation, for example, of caspase-3 activation by XIAP, a baseline level of caspase-3 activity would be detectable. However, if the agent can modulate the regulation of caspase-3 activation by the XIAP, for example, by preventing the inhibitory action of XIAP, an increase from the baseline level of caspase-3 activity will be detectable. Activation, or inhibition of activation, of the caspase can be detected using any of the methods disclosed herein, including, for example, by detecting hydrolysis of a substrate that is specifically hydrolyzed by the caspase or by detecting formation of the active caspase by immunoblot analysis. The processed caspase also can be detected by ELISA or RIA using antibodies that react with epitopes present in the processed and active caspase, but not in the pro-caspase.

The methods of the invention are exemplified by the modulation of caspase-3, caspase-7 and caspase-9 activity by XIAP. However, any IAP, including any eIAP, can be used in an assay in combination with the appropriate caspase. For example, c-IAP-1 and c-IAP-2 also inhibit caspase-3, caspase-7, and caspase-9 in vitro (see Examples IV and IX) and, therefore, also are useful in a method of the invention. Other IAP proteins that are involved in regulating particular caspases can be identified using the methods disclosed herein, then the particular combination of caspase and IAP can be used in a screening assay to identify an agent that modulates the regulation of caspase activation by the IAP or that alters the specific association of the IAP and caspase. Thus, the following examples are intended to illustrate but not limit the present invention.

Example I

XIAP Inhibits Caspase Activity and Nuclear Degradation in a Cell-Free System

This example demonstrates that XIAP inhibits apoptotic-like destruction of isolated nuclei in cytosolic extracts and binds to and inhibits the activation of caspase-3 and caspase-7.

A. Plasmid Constructs:

A cDNA molecule encoding XIAP was obtained by RT-PCR using a first strand cDNA derived from Jurkat T cells as the template and specific primers based upon Genbank accession number U32974 (forward primer, 5'-GGGAATTCAT-GACTTTTAACAGTTTTGAAGGAT-3' (SEQ ID NO: 4); reverse primer, 5'-CTCTCGAGCATGCCTACTATAGAGT-TAGA-3' (SEQ ID NO: 5)). The PCR product was digested with Eco RI and Xho I, then ligated into pcDNA3 (Invitrogen, Inc.; La Jolla Calif.), which contains an N-terminal Myc tag, or into pGEX4T-1 (Pharmacia; Piscataway N.J.), to produce pGEX4T-1-XIAP.

Plasmid pGEX4T-1-XIAP was introduced into E. coli strain BL21 (DE3) containing the plasmid, pT-Trx (Yamakawa et al., J. Biol. Chem. 270:25328-25331 (1995), which is incorporated herein by reference). Expression of the GST-XIAP fusion protein was induced with 0.2 mM IPTG at 30° C. for 3 hr. The GST-XIAP fusion protein was obtained from the soluble fraction, affinity purified using glutathione-Sepharose and dialyzed against phosphate buffered saline (PBS).

cDNA molecules encoding full length caspase-3, caspase-6 and caspase-7 and a cDNA encoding the catalytic subunit of caspase-8 (Ser 217 to the C-terminus) were subcloned into pET vectors (Novagen, Inc.; Madison Wis.), expressed in E. coli strain BL21 (DE3) pLysS as His6-tagged proteins, and purified as described (Muzio et al., J. Biol. Chem. 272:2952-2956 (1997); Orth et al., J. Biol. Chem. 271:20977-20980 (1996), each of which is incorporated herein by reference; Zhou et al., supra, 1997). Recombinant control proteins, GST-Bcl-2, GST-Bax, GST-CD40 cytosolic domain, and His6-S5a proteasome subunit, were prepared as previously described (Hanada et al., J. Biol. Chem. 270: 11962-1196 (1995); Sato et al., FEBS Lett. 358:113-118 (1995); Deveraux et al., J. Biol. Chem. 270:29660-29663 (1995), each of which is incorporated herein by reference).

B. Cell-Free Assays:

1. Preparation of Cytosolic Extracts

The cytosol fraction of cell extracts was prepared from 293 embryonic kidney cells or Jurkat T cells, essentially as described (Liu et al., supra, 1996), but with modifications as indicated below. Cells were washed with ice cold buffer A (20 mM Hepes (pH 7.5), 10 mM KCl, 1.5 mM $MgCl_2$, 1 mM EDTA, 1 mM DTT and 0.1 mM PMSF) and suspended in 1 vol buffer A, then incubated on ice for 20 min. 293 cells were disrupted by passage 15× through a 26 gauge needle and Jurkat T cells were disrupted by dounce homogenization in 2 ml using 15 strokes with a pestle B. Cell extracts (10-15 mg total protein/ml) were clarified by centrifugation at 16,000×g for 30 min, then the NaCl concentration was increased by 50 mM. Cytosolic fractions were used immediately or stored frozen at −80° C.

2. Apoptosis of Nuclei in Cell-Free System

Isolated nuclei were prepared from HeLa cells (Martin et al., supra, 1995). Approximately $5 \times 10^4$ to $1 \times 10^5$ nuclei were added to 20 µl cytosolic extract and apoptosis was initiated by adding 10 µM horse heart cytochrome c (Sigma, Inc.; St.

Louis Mo.) and 1 mM dATP, alone (positive control) or with cytochrome c, dATP and either 0.4 μM GST-XIAP or 0.4 μM GST-Bcl-2. Following incubation at 37° C. for 60 min., nuclei were stained with 1 μg/ml of acridine orange and ethidium bromide and the percentage of nuclei with apoptotic features, including extremely condensed chromatin and the genesis of fragmentation of nuclei, was determined.

Nuclei incubated in cytosolic extract, alone, showed a baseline level of about 15% apoptotic nucleic (average of two experiments). Addition to the cytosolic extract of cytochrome c and dATP, which activate caspases (see below; see, also, Liu et al., supra, 1996), increased the level of apoptotic nuclei to greater than 95%, whereas addition of cytochrome c and dATP to the nuclei, alone (no cytosolic extract), had no effect. Addition of GST-Bcl-2 simultaneously with cytochrome c and dATP had no effect as compared to the level of apoptosis observed when cytochrome c and dATP, alone, were added to the extract (greater than 95% apoptotic nuclei). In contrast, addition of GST-XIAP with cytochrome c and dATP to the cytosolic extract resulted in only the baseline level of apoptotic nuclei (approximately 15%) observed in extracts to which cytochrome c and dATP had not been added. These results indicate that nuclei can be induced to undergo changes characteristic of apoptosis in the cell-free system and that XIAP prevents apoptosis of the nuclei in this system.

3. Activation of Caspases in Cell-Free System

Caspase activity was assayed by release of either 7-amino-4-trifluoromethyl-coumarin (AFC) or p-nitroanilide (pNA) from benzylyoxycarbonyl-DEVD (SEQ ID NO: 2) or benzylyoxycarbonyl-YVAD (SEQ ID NO: 3) synthetic peptides using a Molecular Devices Spectromax 340 for AFC labeled peptides or Perkin/Elmer LS50B for pNA labeled peptides (see Example II; see, also, Zhou et al., supra, 1997). Cytosolic extracts from 293 cells or Jurkat T cells were used directly (negative control) or were treated with 1 μM cytochrome c and 1 mM dATP or with cytochrome c, dATP and 0.2 μM GST-XIAP. Additional control reactions were performed by substituting 2 μM GST-Bcl-2, GST-Bax, GST-NM23 or GST-CD40 cytosolic domain, or 5 μM $His_6$-S5a protein for GST-XIAP. DEVD-pNA hydrolysis was measured at various times and multiple experiments were performed using several different GST-XIAP preparations.

In experiments using 293 cell extracts, a low level of DEVD-pNA hydrolysis activity was observed in the control untreated cytosolic extract; DEVD-pNA hydrolysis was barely evident after 5 min and showed an $\Delta A405 \approx 0.01$ after 15 min. In extracts treated with cytochrome c and dATP, either alone or in combination with GST-Bcl-2, GST-Bax, GST-NM23, GST-CD40 cytosolic domain, or $His_6$-S5a, DEVD-pNA hydrolysis was evident within 5 min and increased exponentially during the 15 min time period examined ($\Delta A405 \approx 0.1$ after 15 min). In contrast, in 293 cell extracts treated with cytochrome c, dATP and XIAP, DEVD-pNA hydrolysis was approximately the same as untreated control extracts, which were not incubated with cytochrome c.

Similar results were obtained using cytosolic extracts prepared from Jurkat cells, except that the level of DEVD-pNA hydrolysis in control untreated extracts steadily, but slowly, increased during the 20 min time period examined ($\Delta A405 \approx 0.02$ after 15 min; $\Delta A405 \approx 0.025$ after 20 min). In extracts treated with cytochrome c and dATP, either alone or in combination with GST-Bcl-2, GST-Bax, GST-NM23, GST-CD40 cytosolic domain, or $His_6$-S5a, DEVD-pNA hydrolysis again was evident within 5 min, increased linearly for about 15 min ($\Delta A405 \approx 0.09$), then began to level off ($\Delta A405 \approx 0.1$ after 20 min). In comparison, DEVD-pNA hydrolysis in extracts treated with cytochrome c, dATP and XIAP increased in parallel with, but slightly higher than, that of the control extracts ($\Delta A405 \approx 0.025$ after 15 min; $\Delta A405 \approx 0.03$ after 20 min). These results indicate that cytochrome c and dATP induce DEVD-pNA hydrolytic activity in cytosolic extracts prepared from two different cell types and that XIAP inhibits the activation of this hydrolytic enzyme.

In order to determine whether endogenously expressed XIAP had the same effect as exogenously added XIAP, cytosolic extracts were prepared from 293 cells that were transiently transfected with pcDNA3-XIAP, which expresses XIAP, or with the control pcDNA3 plasmid. Cytochrome c/dATP-induced activation of DEVD-pNA hydrolyzing activity was reduced by greater than 50% in extracts prepared from the cells transfected with pcDNA-XIAP as compared to the control plasmid. These results confirm that XIAP inhibits activation of the hydrolytic enzyme and demonstrate that such inhibition occurs whether XIAP is added to the extract or is expressed in cells from which the extract is prepared.

Immunoblot analysis was performed to confirm that DEVD-pNA hydrolysis was due to activation of a caspase. Antiserum specific for XIAP was prepared in rabbits using the synthetic peptide, $NH_2$-CDAVSSDRNFPNSTNL-PRNPS-amide (SEQ ID NO: 6), which represents amino acid positions 241 to 261 of XIAP (Liston et al., supra, 1996; Duckett et al., supra, 1996), conjugated to maleimide-activated KLH or OVA carrier proteins (Pierce, Inc.; Rockford Ill.). Anti-caspase-3 antibody was prepared as described by Krajewski et al. (*Cancer Res.* 57:1605-1613 (1997), which is incorporated herein by reference). Purified caspases were prepared from cloned cDNA molecules and purified by standard metal chromatography (Zhou et al., supra, 1997).

Immunoblot analysis was performed using untreated 5 μl cytosolic extracts (10 mg/ml) or extracts incubated for 0.5 or 1 hr with cytochrome c and dATP or with active caspase-8 (1 μg), and in the absence or presence of 0.2 μM GST-XIAP (30 μl reaction vol). Cytosolic extracts were normalized for protein content, then 5 μl (10 mg/ml) was fractionated in 750 mM Tris/12% polyacrylamide/0.1% SDS gels and transferred to nitrocellulose (Deveraux, supra, 1995); Orth et al., supra, 1996).

Three major caspase related bands (referred to herein as bands 1, 2 or 3) were observed: the highest molecular mass band (band 1; 32 kDa) represents unprocessed pro-caspase-3; the intermediate band (band 2; 22-24 kDa) represents the partially processed pro-caspase-3 (large subunit and pro-domain); and the lowest bands (band 3; 17-20 kDa) represent two versions of the fully processed large subunit, active caspase-3; the anti-caspase-3 antibody does not react with the 10-11 kDa small subunit of the processed protease. Probing of the blot with anti-XIAP antiserum revealed the presence of XIAP in the appropriate samples.

Band 1, the unprocessed pro-caspase-3, was present in each sample, although to a greater or lesser extent depending on the particular treatment, and was the only band observed in control cytosolic extracts (no treatment). Band 3 (active caspase-3) was the primary band observed in extracts treated with cytochrome c and dATP or with caspase-8. However, when XIAP protein was added to extracts prior to addition of cytochrome c and dATP, most of the caspase-3 represented unprocessed pro-caspase-3 (band 1). In contrast, in extracts treated with caspase-8 and XIAP, band 2 was the primary band observed, with little or no band 3 (active caspase-3) present. These results indicate that the DEVD-pNA hydrolytic activity correlates with the processing of pro-caspase-3 to active caspase-3 and that the inhibition of DEVD-pNA hydrolytic activity by XIAP correlates with the inhibition of processing of pro-caspase-3 to active caspase-3. The results also indicate that XIAP inhibits the activation of caspase-3 by preventing the completion of caspase-3 processing, consistent with direct inhibition of this caspase, since removal of the pro-domain occurs through an autocatalytic mechanism (Martin et al., supra, 1995).

Example II

XIAP Selectively Inhibits the Activation of Caspase-3 and Caspase-7 and Binds to These Caspases This example demonstrates that XIAP inhibits the activation of caspase-3 and caspase-7, but not of caspases-1, 6 or 8 and that XIAP specifically associates with caspase-3 and with caspase-7 in vitro.

Purified recombinant caspase-1, caspase-3, caspase-6, caspase-7 or caspase-8 were incubated with DEVD-pNA, either alone or with a 10-fold to 50-fold molar excess of GST-XIAP (20 µM) and substrate hydrolysis was measured. Purified active caspase concentrations ranged from 0.1 nM to 10 nM. XIAP concentration ranged from 0.1 nM to 500 nM. Assays were performed in caspase buffer (50 mM Tris, pH 7.4, 100 mM NaCl, 10% sucrose, 5-10 mM DTT, 1 mM EDTA and 0.1% CHAPS).

Purified GST-XIAP inhibited processing of DEVD-pNA in vitro by caspase-3 and by caspase-7 by greater than 95% when present at a 10-fold molar excess, but did not interfere with substrate cleavage by caspase-1, caspase-6 or caspase-8, even when added at a 50-fold molar excess. Furthermore, a GST fusion protein containing only the three BIR domains of XIAP (amino acids 1-337) potently inhibited caspase-3 and caspase-7 in vitro, whereas a GST fusion protein containing the RING domain (amino acids 338-497) had no effect. Addition of GST-CD40 had no effect on caspase activity. These results indicate that XIAP selectively prevents the activation of caspase-3 and caspase-7.

In addition to inhibiting proteolytic activity of caspase-3 and caspase-7 in vitro, XIAP also bound directly to these caspases in vitro. GST-XIAP (3 µg) or GST-CD40 (6 µg) was immobilized on 5 µl glutathione-SEPHAROSE beads, then added to 50 µl 293 cell cytosolic extract that either was untreated ("control") or was preincubated with 1 µM cytochrome c and 1 mM dATP for 60 min at 30° C., or was incubated with 0.5 µg purified caspase-3, caspase-6 or caspase-7 in 100 µl of caspase assay buffer (Martin et al., supra, 1995) containing 0.1% (w/v) bovine serum albumin. Following incubation at 4° C. for 60 min, the beads were removed by centrifugation and washed twice with 100 vol 50 mM Tris (pH 7.5), 150 mM KCl, 2 mM DTT and 0.025% Triton-X100, then subjected to SDS-PAGE and immunoblot assay (see Example I.B.3).

Specific binding of caspase-3 and caspase-7, but not caspase-6, was observed following incubation of the extract with the GST-XIAP beads. No caspase binding was observed with the GST-CD40 beads. In other experiments, GST-XIAP did not efficiently bind unprocessed pro-caspase-3 or pro-caspase-7 present in cytosolic assays, but bound the processed caspase-3 and caspase-7 following treatment of the extracts with cytochrome c and dATP. In addition, the partially processed caspase-3 produced by incubation of cytosolic extracts with caspase-8 and XIAP (see Example I.B.3) efficiently bound GST-XIAP. XIAP also specifically bound to His6-caspase-3 and to His6-caspase-7 immobilized on a Ni-resin. These results indicate that XIAP directly binds active caspase-3 and active caspase-7, as well as the partially processed pro-caspase-3 comprising the large subunit and pro-domain, but does not bind the unprocessed pro-caspases.

Equilibria were determined from progress curves when substrate hydrolysis reached a steady-state; slopes were calculated by curve fit analysis using the cricket graph program. Experiments were performed using purified recombinant caspase-3, caspase-6, or caspase-7. DEVD-AFC hydrolysis was measured using 0.1 nM caspase and a range of concentrations (0.2 to 12 µM) of recombinant XIAP (rXIAP). The inhibition constant ($K_i$) was calculated without any assumption of the inhibitory mechanism and, therefore, without adjustment for the 0.1 mM DEVD-AFC substrate concentration (Zhou et al., supra, 1997). Average ratio velocities ($v_i/v_o$, where "$v_i$" indicates presence of GST-XIAP and "$v_o$" indicates absence of GST-XIAP) were determined.

Average ratio velocities less than 0.2 were obtained with caspase-3 and caspase-7, indicating that XIAP significantly inhibited caspase-3 and caspase-7 mediated DEVD hydrolysis. In contrast, ratios of about 1.0 were obtained with caspase-6 and caspase-8, indicating no difference in DEVD hydrolysis in the presence or absence of XIAP. These results indicate that XIAP inhibits caspase-3 and caspase-7 activity in vitro, but has no effect on the ability of caspase-6 or caspase-8 to hydrolyze DEVD-containing peptides.

Progress curve analysis also was used to determine the inhibition constants ($K_i$) of XIAP for caspase-3 and caspase-7. XIAP exhibited tight, reversible binding to caspase-3 ($K_i \approx 0.7$ nM) and to caspase-7 ($K_i \approx 0.2$ nM). These values compare favorably with viral inhibitors of caspases, including cowpox CrmA ($K_i \approx 0.01$-$0.95$ nM) and baculovirus p35 ($K_i \approx 1.0$ nM) for their target caspases (see Zhou et al., supra, 1997; Bertin et al., supra, 1996).

Example III

XIAP Prevents Caspase Activation in Cells

This example demonstrates that XIAP inhibits Bax-induced caspase-3 processing and cell death in 293T cells, which are 293 cells that contain the SV40 large T antigen.

Subconfluent 293T cells were transfected with 1 µg pcDNA3-human Bax and either 9 µg pcDNA3 (control plasmid) or 9 µg pcDNA3-Myc-XIAP in 6 cm dishes using a calcium phosphate method. N-benzyloxycarbonyl-Val-Ala-Asp fluoromethylketone (zVAD-fmk; 50 µM) (Bachem California; Torrance Calif.) was added immediately after transfection of the Bax plasmid. Transfection efficiency was uniformly 80-90%, as determined by X-Gal staining following cotransfection with pCMV-βGal.

Cells were maintained in culture for 24 hr, then floating and attached cells were harvested and an aliquot was removed and the percent of dead cells was determined by either trypan blue or propidium iodide (PI) dye exclusion assay. A second aliquot was used to assess the percentage of apoptotic cells with subdiploid DNA content by FACS analysis of PI stained, ethanol fixed cells. The remaining cell pellets were lysed in 10 mM HEPES (pH 7.5), 142 mM KCl, 1 mM EGTA, 1 mM DTT, 0.2% NP-40, 0.1 mM PMSF and used for immunoblot analysis or for protease assays.

PI staining revealed a control level of about 2% apoptotic cells (control plasmid transfected cells) and about 5% apoptotic cells in the XIAP expressing cells. Expression of Bax in the cells increased the level of apoptotic cells to about 25%. In comparison, expression of XIAP in combination with Bax significantly reduced the level of apoptotic cells to less than about 10% (p<0.01; t-test). Similarly, expression of a myc tagged version of XIAP containing only the BIR domains was as effective as the full-length protein at suppressing Bax-induced apoptosis, whereas the RING domain of XIAP had no effect. Treatment of Bax expressing cells with the caspase inhibitor zVAD-fmk reduced the level of apoptosis to about 5%.

These results indicate that XIAP inhibits caspase activation in living cells. Furthermore, the ability of the BIR expressing construct to inhibit apoptosis demonstrates that the inhibitory activity of XIAP correlates with the ability of XIAP to bind a caspase.

DEVD-AFC hydrolysis assays and immunoblot analysis revealed that extracts prepared from Bax transfected 293T cells contained substantially higher amounts of caspase activity and processed caspase-3 compared to control transfected cells. In contrast, analysis of extracts from cells cotransfected with Bax and XIAP revealed that XIAP markedly inhibited Bax-induced generation of caspase activity and pro-caspase-3 processing. This suppression of pro-caspase-3 processing in cells and in cytosolic extracts in vitro indicates that XIAP either blocks the activity of caspases upstream of caspase-3 or prevents caspase-3-mediated processing of pro-caspase-3, thus preventing an auto-amplification process, whereby a small amount of processed and active caspase-3 cleaves and activates additional pro-caspase-3.

Example IV c-IAP-1 and c-IAP-2 Selectively Bind to Caspase-3 and Caspase-7 and Inhibit the Activity of These Caspases This example demonstrates that c-IAP-1 and c-IAP-2, like XIAP, bind to caspase-3 and caspase-7, inhibit the processing of pro-caspase-3 and pro-caspase-7 to the active caspases, and inhibit caspase-3 and caspase-7 activity.

c-IAP-1 and c-IAP-2 cDNA sequences were obtained by RT-PCR of RNA obtained from Jurkat T cells. The following PCR primers were used:

5'-AGGGAATTCATGCACAAAACTGCCTCCCA-3' (c-IAP-1 forward primer; SEQ ID NO: 7); 5'-CTCCTCGAG-GATGGCTTCAAGTGTTCAAC-3' (c-IAP-1 reverse primer; SEQ ID NO: 8);

5'-AGGGAATTCATGAACATAGTAGAAAACAGCA-3' (c-IAP-2 forward primer; SEQ ID NO: 9); and 5'-CTCCTCGAGAGATGATGTTTTGGTTCTTCTT-3' (c-IAP-2 reverse primer; SEQ ID NO: 10). PCR products were digested with Eco RI and Xho I and ligated into pGEX4T. c-IAP-1 (BIR) and c-IAP-2 (BIR) constructs were generated by PCR of the full length constructs using the same forward primers and the following reverse primers:

5'-CTCCTCGAGGATCTAACCTTGAATCT-CATCAACAAAC-3' (c-IAP-1; SEQ ID NO: 11); and 5'-CTCCTCGAGGATCTACTTGAACTTGACG-GATGATGAAC-3' (c-IAP-2; SEQ ID NO: 12).

All c-IAP constructs were expressed in E. coli strain BL21 (DE3) containing the plasmid pT-Trx (see Example I.A). E. coli was grown at 30° C. to an optical density of 0.5; fusion protein expression was induced at 30° C. with 0.4 mM IPTG for 2 hr, except that GST-c-IAP-2 expression was induced for 1 hr at room temperature. Fusion proteins were obtained from the soluble fraction and affinity purified on glutathione-SEPHAROSE by standard methods. Eluted proteins were dialyzed against PBS.

Caspase activity was determined essentially as described in Example II, using the benzyloxycarbonyl-DEVD-AFC (SEQ ID NO: 2) substrate and was assayed at 37° C. using the Perkin-Elmer LS50B fluorometric plate reader in the kinetic mode with excitation and emission wavelengths of 400 nm and 505 nm, respectively. Inhibition rates and equilibria were calculated from progress curves, where substrate hydrolysis (100 µM) was measured in the presence of caspase-3 (7 pM), caspase-6 (100 pM), caspase-7 (150 pM) or caspase-8 (125 pM) and a range of IAP concentrations for 0.025 to 1.5 µM. Reactions were performed in caspase buffer (50 mM Hepes, 100 mM NaCl, 1 mM EDTA, 0.1% CHAPS, 10% sucrose, 5 mM DTT). The inhibition constant, $K_i$, was calculated as described (Zhou et al., supra, 1997). Immunoblot analysis was performed as described in Example I.B.3.

Like XIAP, c-IAP-1 and c-IAP-2, as well as constructs comprising the BIR domains of these IAP proteins, also inhibited caspase-3 and caspase-7 activity in in vitro assays. $K_i$ for caspase-3 was as follows: c-IAP-1 ($K_i$ 120 nM); c-IAP-1 (BIR) ($K_i$ 330 nM); c-IAP-2 ($K_i$ 40 nM); and c-IAP-2 (BIR) ($K_i$ 260 nM); and $K_i$ for caspase-7 was as follows: c-IAP-1 ($K_i$ 53 nM); c-IAP-1 (BIR) ($K_i$ 160 nM) c-IAP-2 ($K_i$ 26 nM); and c-IAP-2 (BIR) ($K_i$ 238 nM). In addition, GST constructs of c-IAP-1, c-IAP-1 (BIR), c-IAP-2 and c-IAP-2 (BIR), as well as NAIP, bound caspase-3 and caspase-7 in vitro, as demonstrated using the glutathione-SEPHAROSE affinity chromatography (see Example II), whereas the caspases did not bind to a control GST-CD40 construct.

The c-IAP proteins also inhibited caspase activity in the cell-free assays. Addition of 3 µM c-IAP-1, c-IAP-1 (BIR), c-IAP-2 or c-IAP-2 (BIR) to 293 cell cytosolic extracts activated for 30 min with cytochrome c and dATP inhibited DEVD hydrolysis. Furthermore, as demonstrated for XIAP, immunoblot analysis confirmed that the inhibition of caspase activity correlated, in part, with inhibition of processing of pro-caspase-3 and pro-caspase-7 to caspase-3 and caspase-7, respectively.

These results demonstrate that IAP proteins can bind to and inhibit the activity of caspases and confirm the general regulatory effect that IAP proteins have with respect to the caspases.

Example V

XIAP Differentially Inhibits Processing and Activation of Pro-Caspase-3 in Extracts Treated with Caspase-8 as Compared to Extracts Treated with Cytochrome C This example demonstrates that XIAP differentially inhibits processing and activation of pro-caspase-3 in extracts treated with caspase-8 as compared to cytochrome c.

In a cell-free system, the addition of exogenous active caspase-8 or cytochrome-c to cytosolic extracts can induce proteolytic processing of pro-caspase-3 (Liu et al., supra, 1996; Muzio et al., supra, 1997). Caspase-8 induced proteolytic processing of pro-caspase-3 into its characteristic p20 and p17 forms. The small p12 subunit of caspase-3 was undetectable with the anti-caspase-3 antibody used for these studies.

The cowpox CrmA protein is a serpin that binds tightly and potently inhibits the proximal cell death protease caspase-8, but is far less active against caspase-3 and other downstream effector caspases (Komiyama et al., J. Biol. Chem. 269: 19331-19337 (1994); Orth and Dixit, J. Biol. Chem. 27:8841-8844 (1997); Srinivasula et al., Proc. Natl. Acad. Sci., USA 93:14486-14491 (1996); Zhou et al., supra, 1997). As a control, recombinant purified CrmA was added to the extracts concurrently with active caspase-8. Addition of recombinant CrmA completely prevented caspase-8 induced processing of pro-caspase-3. However, subsequent addition of cytochrome c and dATP bypassed the CrmA-mediated inhibition of pro-caspase-3 processing (FIG. 1A). Relatively large quantities of CrmA (10 µM) failed to substantially suppress the cytochrome c-induced processing of pro-caspase-3, whereas 0.1 µM of CrmA completely inhibited caspase-8-induced processing of pro-caspase-3. Thus, CrmA is a relatively potent inhibitor of caspase-8 induced processing of pro-caspase-3, but is far less effective against the cytochrome c-mediated activation of pro-caspase-3. In contrast, addition of 0.1-0.2 µM recombinant XIAP effectively abolished cytochrome c-induced processing of pro-caspase-3 in cytosolic extracts. Similar results were obtained when caspase activity was assayed in cytosolic extracts by measuring the rate of Ac-DEVD-AFC hydrolysis (FIG. 1B). These results indicate that caspase-8 is upstream or independent of the cytochrome c pathway and further demonstrate that XIAP functions downstream of cytochrome c by inhibiting pro-caspase-3 processing, consistent with previous studies.

For the CrmA and XIAP inhibition of caspase-8 and cytochrome c-induced processing and activation of pro-caspase-3 shown in FIG. 1A 0.1 µM recombinant purified active caspase-8 was added to cytoplasmic extracts from 293 cells in the absence or presence of 0.5 µM CrmA; 10 µM cytochrome c and 1 mM dATP; or 0.2 µM XIAP. Samples were incubated at 30° C. for 30 minutes. Extracts were then separated by SDS-PAGE electrophoresis, transferred to nitrocellulose and incubated with antisera specific for the zymogen and large subunit of caspase-3.

For caspase activation in cytosolic extracts, cytosolic extracts were prepared using 293 embryonic kidney cells essentially as described in Liu et al., supra, 1996, with several modifications as follows. Briefly, cells were washed with ice-cold buffer A (20 mM Hepes [pH 7.5], 10 mM KCl, 1.5 mM $MgCl_2$, 1 mM EDTA, and 1 mM DTT) and suspended in 1 volume of buffer A. Cells were incubated on ice for 20 minutes and then disrupted by passage through a 26 gauge needle 15 times. Cell extracts were clarified by centrifugation at 16,000×g for 30 minutes and the resulting supernatants were stored at –80° C. For initiating caspase activation, either 10 µM horse heart cytochrome c (Sigma, Inc.) together with 1 mM dATP, or 100 nM of purified recombinant caspase-8, was added to extracts (10-15 mg total protein/ml).

DEVD-AFC cleavage activity was analyzed as follows. Briefly, caspase activity was assayed by release of amino-4-trifluoromethyl-coumerin (AFC) or p-nitroanilide (pNA) (Enzyme System Products) from YVAD- or DEVD-containing synthetic peptides using continuous-reading instruments as described previously (Quan et al., *J. Biol. Chem.* 270: 10377-10379 (1995); Stennicke and Salvesen, *J. Biol. Chem.* 272:25719-25723 (1997)). Tetrapeptide inhibitors were purchased from Calbiochem.

Figure 2:
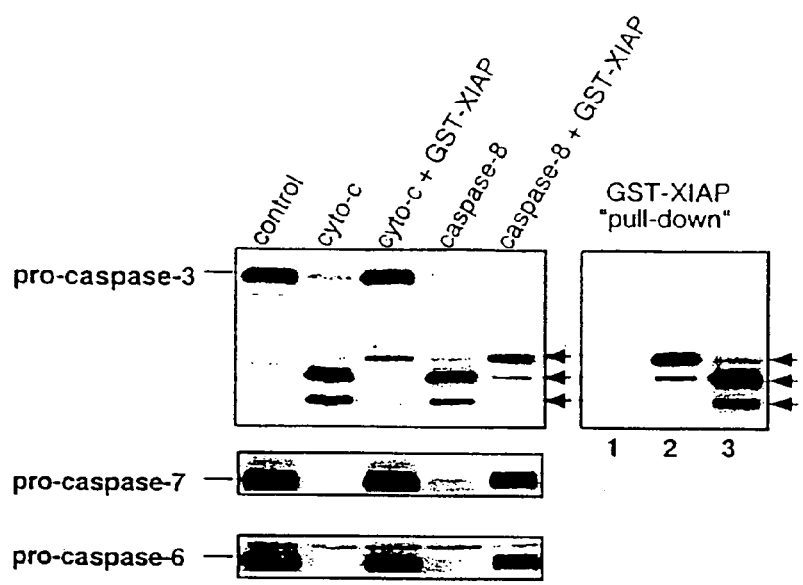
FIG. 2 shows XIAP-mediated inhibition of pro-caspases-3, -6 and -7 processing in cytochrome c and caspase-8 treated extracts. (A) Western analysis with antisera specific for the zymogen and large subunits of caspase-3 (upper left panel) or for the zymogen forms of caspase-7 or -6 (lower left panels). The upper right panel shows immunoblotting using anti-caspase-3 antiserum of extracts containing GST-XIAP incubated with glutathione-Sepharose beads. Lane 1: Glutathione beads incubated with extracts containing cytochrome c, dATP and GST-XIAP. Lane 2: Glutathione beads incubated with extracts containing caspase-8 and GST-XIAP. Lane 3: GST-XIAP glutathione beads incubated with extracts that had been previously treated with cytochrome c and dATP. (B) Percentage of green fluorescent protein positive 293 cells with apoptotic morphology and nuclear changes consistent with apoptosis enumerated by DAPI-staining (mean+SD; n=3) at 36 hrs. The right panel shows immunoprecipitation of cell lysates using anti-myc monoclonal antibody with protein-G-Sepharose, followed by SDS-PAGE immunoblot analysis using anti-caspase-3 antiserum. Lane 1: control plasmid. Lane 2: myc-XIAP. Lane 3: Fas and myc-control. Lane 4: Fas plus myc-XIAP. (C) Schematic of XIAP-mediated inhibition of either caspase-8 or cytochrome c induced activation of pro-caspases-3, -6 and -7.
Figure 2:
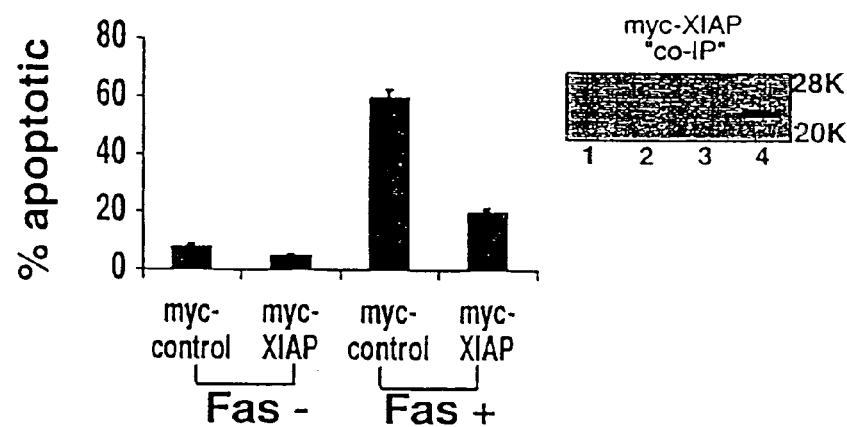
Figure 2:
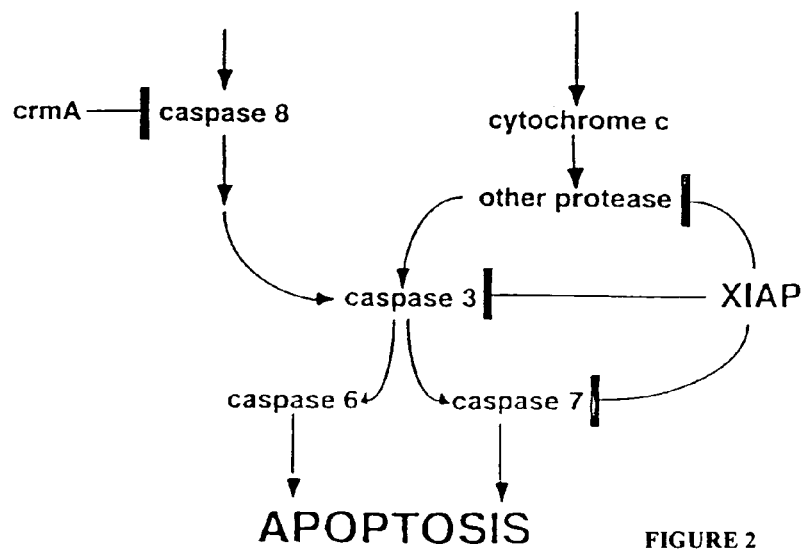

Using immunoblot analysis, the processing of pro-caspase-3, pro-caspase-6 and procaspase-7 was studied in caspase-8 and cytochrome c-induced extracts in the presence or absence of recombinant XIAP (FIG. 2). Addition of either cytochrome c with dATP, or active caspase-8, to cytosolic extracts in the absence of XIAP resulted in the proteolytic processing of caspases-3, -6 and -7, as indicated by the conversion of their zymogen forms. In contrast, addition of XIAP to cytochrome c treated extracts inhibited processing of the three pro-caspases. As shown in FIG. 2A, most of caspase-3 remained in the unprocessed form (~36 kDa) in cytochrome c treated extracts containing XIAP, although a small amount of the large subunit of caspase-3 was detected. In extracts treated with caspase-8, processing of pro-caspase-6 and pro-caspase-7 was also blocked by XIAP; however, pro-caspase-3 was cleaved into large and small subunits. As shown in FIG. 2A, the ~36 kDa zymogen of caspase-3 was almost completely consumed while a ~24 kDa form of the large subunit of caspase-3 accumulated. Little or none of the mature ~20 kDa and ~17 kDa forms of the caspase-3 large subunit were evident in extracts treated with caspase-8 and XIAP (FIG. 2A).

Processing of pro-caspase-3 involves an initial cleavage that generates the p12 small subunit, and a partially processed p24 large subunit (Martin et al., *EMBO J.* 15:2407-2416 (1996)). The p24 large subunit is further processed by autocatalytic removal of its N-terminal pro-domain to generate either p20 or p17 forms of the large subunit (Martin et al., supra, 1996). As described above, the partially processed p24 form accumulated in the caspase-8 and XIAP treated extracts. These results indicate that XIAP blocked only the autocatalytic processing of the large subunit of caspase-3 and did not inhibit the initial cleavage of pro-caspase-3 by caspase-8. In contrast, in cytochrome c treated extracts, XIAP strongly suppressed the initial processing of pro-caspase-3 into large and small subunits.

In order to analyze whether processed caspase-3 was bound to XIAP, GST-XIAP protein was recovered from the extracts described above using glutathione-Sepharose, (FIG. 2A right panel; lane 1). In cytochrome c-treated extracts, no caspase-3 molecules were associated with GST-XIAP protein. In contrast, in extracts treated with caspase-8, GST-XIAP predominantly bound the p24 form of the large subunit of caspase-3 (FIG. 2A, lane 2). As a control, GST-XIAP was added to extracts that had previously been treated with cytochrome c for 1 hr and then recovered on glutathione-Sepharose (lane 3), demonstrating that active caspase-3 bound to GST-XIAP, and that most of the large subunit of caspase-3 had been processed to p17 and p20 forms with only a small proportion of the partially processed p24 form present. Similar results were obtained when GST-c-IAP-1 or GST-c-IAP-2 was substituted for GST-XIAP.

XIAP also bound to the p24 form of partially processed caspase-3 in cells over-expressing Fas (CD95), a known activator of caspase-8. As shown in FIG. 2B, Fas-induced apoptosis was markedly suppressed in 293 cells co-transfected with plasmids encoding Fas and myc-epitope tagged XIAP. Immunoprecipitation of myc-XIAP protein from lysates obtained from Fas-overexpressing 293 cells revealed associated p24-caspase-3 (FIG. 2B; right panel; lane 4). In contrast, in cells overexpressing Bax, which induces cytochrome c release from mitochondria, (Rosse et al., *Nature* 391:496-499 (1998)), pro-caspase-3 processing was completely prevented, and no forms of processed caspase-3 were co-immunoprecipitated with XIAP.

In sum, little or no processing of caspases-3, -6 and -7 occurs in cytochrome c treated cells in the presence of XIAP, indicating that XIAP inhibits the cytochrome c pathway upstream of these caspases. In contrast, XIAP inhibits the caspase-8 apoptotic pathway at the level of caspase-3, allowing caspase-8 to induce processing of caspase-3 but preventing the subsequent autocatalytic maturation by directly binding to and inhibiting the partially processed enzyme. These results also indicate that caspases-6 and -7, which remain mostly in their zymogen forms in the presence of XIAP, can be downstream of caspase-3 in the caspase-8 apoptotic pathway.

As illustrated in FIG. 2C, caspase-8 and cytochrome c can activate pro-caspase-3 independently, with each pathway inhibited by XIAP at distinct points. The results described above indicate that XIAP blocks the caspase-8-induced apoptotic program by directly inhibiting caspase-3, thereby preventing the activation of downstream caspases-6 and -7. The results described above also indicate that XIAP inhibits another protease that lies upstream of caspases-3, -6 and -7 in the cytochrome c apoptotic program.

For the XIAP-mediated inhibition of pro-caspase-3, -6 and -7 processing in cytochrome c and caspase-8 treated extracts shown in FIG. 2A, cytochrome c (10 μM) together with dATP (1 mM) or active caspase-8 (0.1 μM) were added to cytosolic extracts from 293 cells with or without GST-XIAP (0.2 μM). Extracts were incubated at 30° C. for 1 hr and then analyzed by immunoblot analysis for the zymogen and large subunits of caspase-3 or for the zymogen forms of caspases-7 and -6. For some analyses, samples of extracts containing GST-XIAP were also incubated with glutathione-Sepharose beads. Resulting bound proteins were analyzed by SDS-PAGE and immunoblotting using anti-caspase-3 antiserum. In experiments with GST and other control GST-fusion proteins, neither inhibition of caspase processing nor caspase binding was observed.

GST-XIAP, c-IAP-1 and c-IAP-2 were expressed and purified as described (Roy et al., *EMBO J.* 16:6914-6925 (1997)). Control GST proteins used for these experiments and those set forth below included GST nonfusion, various GST fusions such as GST-CD40, GST-Bcl-2, GST-TRAF-3 and a GST-NAIP fusion protein in which the NAIP protein fragment fails to properly fold, as determined by circular dichroism.

GST "pull-down" assays were performed as follows. U937 or 293 cells were cultured in methionine-free RPMI or DMEM containing dialyzed 5% FBS and 50 μCi/ml $^{35}$S-L-methionine for 3 hrs prior to extraction into TBS containing 1% Triton-X100 and 1 mM DTT. Lysates were pre-cleared by addition of glutathione-GST beads and incubation for 1 hr at 4° C. Glutathione beads were then removed by centrifugation and washed two times with TBS containing 1% Triton-100 and 1 mM DTT. Bound proteins were resolved in SDS-PAGE gels.

For determination of apoptotic activity in FIG. 2B, 293 cells in 60 mm dishes were transiently transfected with 6 μg of pcDNA-myc-tag control or pcDNA-myc-XIAP plasmids, and either 2 ug of pCMV5 or pCMV5-Fas plasmid DNA. All transfections included 0.5 ug of pEGFP as a marker and were normalized for total DNA content. The percentage of GFP positive cells with apoptotic morphology and nuclear changes consistent with apoptosis were enumerated by DAPI-staining (mean+SD; n=3) at 36 hrs. Alternatively, cell lysates were prepared, and immunoprecipitates were collected using anti-myc monoclonal antibody with protein-G-Sepharose, followed by SDS-PAGE immunoblot assay using anti-caspase-3 antiserum (Krajewska et al., supra 1997) to reveal the XIAP-associated p24 isoform of partially processed caspase-3. Lanes correspond to cells transfected with: (1) control plasmid; (2) myc-XIAP; (3) Fas plus myc-control; and (4) Fas plus myc-XIAP.

Apoptotic assays were performed as follows. 293 cells were transfected as described above, except that 0.5 μg pEGFP plasmid DNA was included. Both floating and adherent cells were recovered 24-36 hrs later, and the percentage of GFP-positive cells that exhibited apoptotic morphology was determined by staining with 0.1 mg/ml DAPI (Roy et al., supra, 1997).

Co-immunoprecipitations and immunoblot assays were performed as follows. Human embryonic kidney 293T cells were maintained in DMEM supplemented with 10% fetal bovine serum, 1 mM L-glutamine and antibiotics. 2×10$^6$ cells were plated in 10 mm dishes and 24 hr later transiently co-transfected with 2 μg of either pFLAG-CMV2-caspase-9 or pCMV-Fas and 6-8 μg of either pcDNA3myc-XIAP, pcDNA3myc-c-IAP-1, pcDNA3myc-c-IAP-2, or pcDNA3myc-control plasmid DNA by a calcium phosphate precipitation method (Roy et al., supra, 1997). Cells were collected 24-48 hrs later by centrifugation, washed in ice cold PBS and lysed for 20 minutes in lysis buffer (10 mM Hepes, 142 mM KCl, 5 mM MgCl$_2$, 1 mM EGTA, 0.2% NP-40). Lysates were cleared by centrifugation at 16,000×g for 30 minutes. Myc-tagged IAP proteins were immunoprecipitated with 40 μl of anti-myc 9E10 antibody immobilized on Protein G-Sepharose (Santa Cruz) for 2 hrs. Immunoprecipitates were washed 3 times with lysis buffer, and bound proteins separated by SDS-PAGE and analyzed by immunoblotting using antibodies specific for the FLAG epitope (Kodak, Inc.), myc-epitope, or caspase-3.

Immunoblotting for caspases was performed as described above using 750 mM Tris/12% polyacrylamide gels, after normalizing cell lysates for protein. Antisera specific for caspase-3, -6 and -7 were prepared as described previously (Krajewski et al., supra, 1997; Orth et al., supra, 1996; Srinivasula et al., *J. Biol. Chem.* 271:27099-27106 (1996)).

Example VI

IAPs Associate with Caspase-9 in Cytochrome C Treated Cytosolic Extracts

This example demonstrates that XIAP, c-IAP-1 and c-IAP-2 can associate with the zymogen of caspase-9.

To identify the protease that XIAP inhibits in the cytochrome c pathway, cytosolic extracts were prepared from 293 cells cultured in the presence of $^{35}$S-L-methionine. GST-XIAP or various control GST proteins, such as GST-TRAF-3, were then added to the metabolically labeled extracts and subsequently recovered using glutathione-Sepharose. As shown in FIG. 3A, separation of bound proteins by SDS-PAGE revealed an ~50 kDa $^{35}$S-labeled protein that associated specifically with GST-XIAP.

Two known caspases have a molecular mass of ~50 kDa: caspase-2 and caspase-9. Caspase-2 does not appear to be activated in cytochrome containing extracts (Roy et al., supra, 1997). To assay whether caspase-9 can associate with XIAP, pro-caspase-9 was in vitro translated in the presence of $^{35}$S-L-methionine and incubated with GST-XIAP, GST-c-IAP-1, GST-c-IAP-2, or with GST control proteins that fail to prevent caspase activation by cytochrome c (Roy et al., supra, 1997). Each of GST-XIAP, GST-c-IAP-1 and GST-c-IAP-2, but not GST-control proteins, associated with pro-caspase-9 (FIG. 3B). Taken together, these results indicate that XIAP, c-IAP-1 and c-IAP-2 can associate with the zymogen of caspase-9. In contrast, only the active forms of caspase-3 and -7 bind to these IAPs (Roy et al., supra, 1997).

For the results shown in FIG. 3A, GST-XIAP was incubated in lysates from U937 cells that had been cultured in $^{35}$S-L-methionine containing media. Lysates were incubated at 4° C. for 1.5 hrs with GST, GST-TRAF-3 (1-357), or GST-XIAP. Proteins were separated on SDS-PAGE gels and analyzed by autoradiography. The asterisk indicates a background band which was non-specifically recovered with the beads and serves as a loading control. Similar results were obtained using extracts from 293 cells.

For the results shown in FIG. 3B, about 2 μM GST-XIAP, c-IAP-1, c-IAP-2 or a GST-control fusion protein immobilized on glutathione-Sepharose was incubated with 10 μl of reticulocyte lysate containing in vitro translated $^{35}$S-labeled pro-caspase-9. After extensive washing, bound proteins were analyzed by SDS-PAGE and autoradiography. As a positive control, 1.5 µl of the in vitro translated reaction (IVT) was analyzed.

Example VII

IAPs Block Pro-Caspase-9 Processing in Cytosolic Extracts Treated with Cytochrome C This example demonstrates that XIAP, c-IAP-1 and c-IAP-2 can block pro-caspase-9 processing in cytosolic extracts treated with cytochrome c.

Based on the observation the XIAP, c-IAP-1 and c-IAP-2 can bind pro-caspase-9 in vitro, these proteins were assayed for the ability to inhibit activation of pro-caspase-9. Cytochrome c was first added to cytosols and processing of in vitro translated $^{35}$S-pro-caspase-9 analyzed in the presence and absence of IAPs. As shown in FIG. 4, pro-caspase-9 remained unprocessed when incubated with cytosolic extracts; however, upon addition of cytochrome c, pro-caspase-9 was cleaved into fragments characteristic of the active subunits of the enzyme. Addition of XIAP nearly completely abolished pro-caspase-9 processing, and c-IAP-1 and c-IAP-2 also inhibited pro-caspase-9 processing, albeit to a lesser extent. These results demonstrate that, not only is pro-caspase-9 bound by XIAP, c-IAP-1 and c-IAP-2, pro-caspase-9 processing also is inhibited by these IAP family proteins.

For the results shown in FIG. 4, in vitro translated $^{35}$S-labeled pro-caspase-9 was added to cytosolic extracts from 293 cells, and subsequently incubated for 30 min at 30° C. with (lanes 2-6) or without (lane 1) 10 µM cytochrome c and 1 mM dATP in the presence or absence of 0.2 µM GST-IAP proteins or a GST control protein. Cytochrome c induced processing of pro-caspase-9 was subsequently monitored by SDS-PAGE and autoradiography. The positions of the processed subunits of caspase-9 are indicated in FIG. 4 by asterisks.

Example VIII

Reconstitution of Caspase-9 Processing In Vitro

This example demonstrates that IAP family proteins can inhibit caspase-9 processing in an in vitro reconstitution system.

An in vitro reconstitution system was employed to further analyze the effects of IAP family proteins on cytochrome c-induced processing of pro-caspase-9. The in vitro reconstitution system included cytochrome c and dATP, in vitro translated apoptotic protease activating factor-1 (Apaf-1), and $^{35}$S-labeled caspase-9 zymogen. As shown in FIG. 5A, incubation of Apaf-1 with pro-caspase-9 did not result in processing unless cytochrome c and dATP were also present. Addition of XIAP, c-IAP-1 and c-IAP-2 to reactions containing Apaf-1 together with cytochrome c and dATP completely blocked pro-caspase-9 processing. Conversely, various control GST-fusion proteins failed to inhibit the cytochrome c-induced cleavage of pro-caspase-9 under these conditions. The addition of cytochrome c and dATP to pro-caspase-9 in the absence of in vitro translated Apaf-1 revealed no processing of the zymogen (FIG. 5A). Conversely, incubation of Apaf-1 with cytochrome c and the pro-form of caspase-3 in the absence of pro-caspase-9 did not result in activation of pro-caspase-3, establishing the requirement for caspase-9 in this system, consistent with the results of Li et al., supra, 1997; Liu et al., supra, 1996; and Zou et al., supra, 1997.

Unlike the IAPs, recombinant Bcl-X$_L$ protein did not suppress the in vitro processing of pro-caspase-9-induced by the combination of Apaf-1, cytochrome c and dATP (FIG. 5B). BCl-X$_L$ also did not inhibit the cytochrome c-induced activation of caspases in cytosols. (not shown). The same preparation of recombinant BCl-X$_L$ protein, however, was fully functional in ion-channel formation assays using KCl-loaded liposomes (Schendel et al., Proc. Natl. Acad. Sci., USA 94:5113-5118 (1997)) and competent at dimerizing with other Bcl-2 family proteins. Thus, Bcl-X$_L$ does not block pro-caspase-9 processing mediated by cytochrome c and Apaf-1 under these in vitro conditions. These results indicate that Bcl-X$_L$ and Bcl-2 are upstream or at the level of cytochrome c release and are consistent with previous results (Kharbanda et al., supra, 1997; and Kluck et al., EMBO J. 16:4639-4649 (1997)).

For the results shown in FIGS. 5A and 5B, in vitro translated $^{35}$S-labeled pro-caspase-9 and Apaf-1 were incubated individually or together with 10 µM cytochrome c and 1 mM dATP. Processing of pro-caspase-9 in the absence or presence of 0.1 µM of the indicated GST-IAP or 0.1 µM Bcl-X$_L$ was then monitored by SDS-PAGE and autoradiography. Asterisks indicate the position of the processed large subunit of caspase-9. Similar results were obtained when as much as 2 µM BCl-X$_L$ was added to cytochrome c-stimulated cytosolic extracts.

To assay caspase-9 activation in vitro, one microgram of plasmids containing cDNAs encoding pro-caspase-9 (pET21 (b)-Mch-6) or Apaf-1 (pcDNA3-Apaf-1) was in vitro transcribed and translated in the presence of [$^{35}$S]-L-methionine using a coupled transcription/translation TNT kit (Promega) according to manufacturer's instructions. Proteins were desalted and exchanged into Buffer A with Bio-spin P-6 columns (BioRad). Caspase-9 (2 µl) was combined with Apaf-1 (6 µl) and cytochrome c/dATP in a total volume of 10 µl with either Buffer A or an equal volume of GST-XIAP, GST-c-IAP-1, GST-c-IAP-2 or GST-NAIP and incubated for 1 hr at 30° C. The reactions were analyzed by SDS-PAGE and autoradiography. For some experiments, in vitro translated His$_6$-caspase-9 was purified by metal chromatography.

Example IX

XIAP Inhibits Active Caspase-9

This example demonstrates that XIAP is a direct inhibitor of caspase-9.

The ability of XIAP to block pro-caspase-9 processing in cytochrome c and dATP treated cytosols was compared to Ac-DEVD-fmk and zVAD-fmk. Ac-DEVD-fmk and zVAD-fmk are two well characterized caspase inhibitors that have been used extensively to address the role of caspases in cell death (reviewed in Jacobson and Evan, Curr. Biol. 4:337-340 (1994); Martin and Green, supra, 1995; Patel et al., FASEB J. 10:587-597 (1996)). As shown in FIG. 6, XIAP is a more potent inhibitor than either Ac-DEVD-fmk or zVAD-fmk of cytochrome c-mediated processing of pro-caspase-9 in cytosolic extracts. In these assays less than 0.2 µM of recombinant XIAP was typically sufficient to completely abolish processing of pro-caspase-9, whereas at least 5 µM of zVAD-fmk or Ac-DEVD-fmk was required for similar inhibition. XIAP was also about 5 fold more potent than baculovirus p35 protein at inhibiting cytochrome c-induced processing of pro-caspase-9 in these assays.

Recombinant active caspase-9 was purified from E. coli extracts, and IAPs assayed for the ability to directly inhibit its activity. Recombinant caspase-9 was found to be extremely sensitive to dilution. In addition, the fluorogenic tetrapeptides typically used for caspase assays proved to be poor substrates for this enzyme. Recombinant pro-caspase-3 was therefore used as a substrate for monitoring the activity of caspase-9.

Incubation of caspase-9 with purified pro-caspase-3 resulted in proteolytic processing of pro-caspase-3 as determined by immunoblot analysis (FIG. 7A). Addition of an equimolar concentration of XIAP relative to caspase-9 strongly inhibited cleavage of pro-caspase-3. Activity of caspase-9 was also measured in a coupled reaction based on hydrolysis of Ac-DEVD-AFC as a result of caspase-3 activation in vitro. XIAP, c-IAP-1 and c-IAP-2 each efficiently inhibited pro-caspase-3 activation and cleavage of the tetrapeptide substrate, whereas various GST control proteins had no significant effect on pro-caspase-3 activation by caspase-9 (FIG. 7B).

Active caspase-3 is known to cleave and activate pro-caspase-9 (Srinivasula et al., *J. Biol. Chem.* 271:27099-27106 (1996)). To eliminate the possibility of a feedback loop in these experiments, XIAP was tested for inhibition of bacterially produced active caspase-9 using in vitro translated and purified [$^{35}$S]-pro-caspase-9 as a substrate. As shown in FIG. 7C, GST-XIAP protein potently inhibited processing of pro-caspase-9 in these in vitro reactions, whereas GST-control protein had little or no effect. In sum, these results demonstrate that XIAP is a direct inhibitor of caspase-9.

Pro-caspase-9 inhibition by Ac-DEVD-fmk, zVAD-fmk and XIAP was compared as follows. In vitro translated $^{35}$S-labeled pro-caspase-9 was added to cytosolic extracts from 293 cells containing 10 µM cytochrome c and 1 mM dATP. Samples were incubated at 30° C. for 30 minutes in the presence of the indicated concentrations of inhibitors. Proteins were separated on SDS-PAGE gels, dried directly, and exposed to film.

Figure 7:
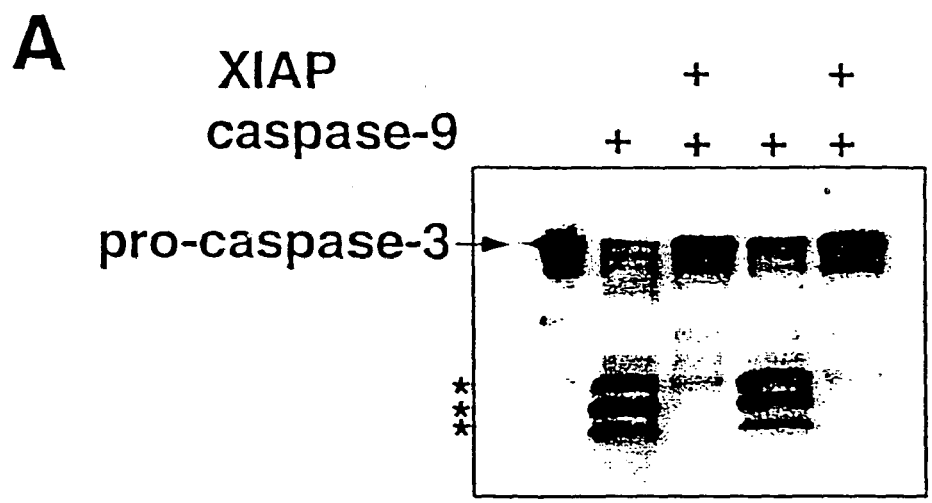
FIG. 7 shows inhibition of purified active caspase-9 by XIAP. (A) Immunoblot analysis of the purified recombinant zymogen form of caspase-3 in the presence or absence of purified His$_6$-tagged active caspase-9 or GST-XIAP. Asterisks denote the processed forms of the large subunit of caspase-3. (B) Release of the AFC fluorophore from DEVD-AFC of the same samples analyzed in A. Activity was arbitrarily designated as 100% for one of two analyzed preparations of active caspase-9. (C) SDS-PAGE and autoradiographic analysis of $^{35}$S-L-methionine-labeled pro-caspase-9 in vitro translated in reticulocyte lysates, purified by metal chromatography, boiled in Laemmli buffer and incubated in the presence or absence of recombinant active caspase-9 with or without GST-XIAP or a GST control protein. The asterisk denotes the processed form of caspase-9.
Figure 7:
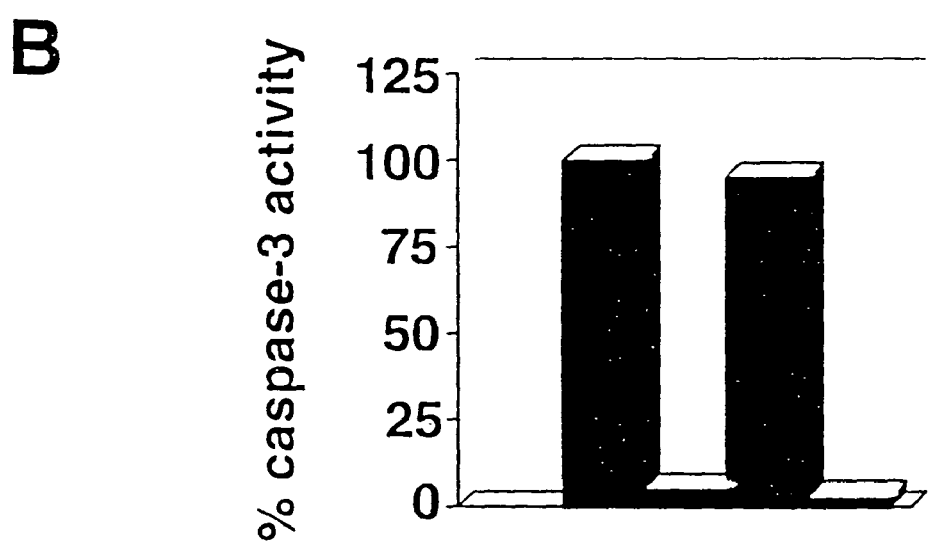
Figure 7:
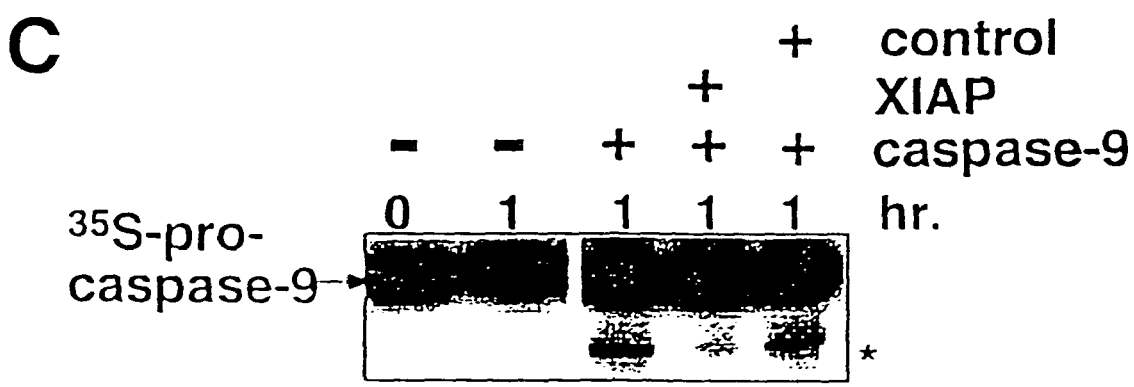

For the results shown in FIG. 7, active caspase-9 was produced in bacteria and purified as a His$_6$-tagged protein. Caspase-9 activity was measured by monitoring the processing and activity of the purified recombinant zymogen form of caspase-3 that was produced in bacteria. Active caspase-9 (0.1 µM) was incubated with pro-caspase-3 (0.5 µM) in the presence or absence of GST-XIAP (0.1 µM). Experiments were performed with two independent preparations of active caspase-9. Samples were subsequently analyzed for pro-caspase-3 processing by immunoblot analysis. Asterisks denote the processed forms of the large subunit of caspase-3. Samples were simultaneously assayed for release of the AFC fluorophore from DEVD-AFC. Activity was arbitrarily designated as 100% for one of the two preparations of active-caspase-9.

Full length N-terminally tagged caspase-9 was subcloned from pcDNA3, Duan et al., *J. Biol. Chem.*, 271:16720-4 (1996), which was provided by Dr. Vishva Dixit, into the NcoI-XhoI (blunt) sites of pET-23d as a NcoI-XbaI (blunt) fragment. The resulting vector was introduced into BL21 (DE3), and fully processed enzyme was obtained when induced by 0.2 mM IPTG at O.D. (600 nm)=0.6 for 4 hours. The zymogen form of caspase-3 was obtained by expression as previously described except that the expression time was reduced to 30 minutes. Pro-caspase-3 and processed caspase-9 were isolated using Ni-chelate Sepharose (Pharmacia, Sweden) chromatography according to the manufacturer's recommendations and eluting with an imidazole gradient from 0-200 mM in 10 mM Tris, 100 mM NaCl, pH 8.0. The concentrations of the purified enzymes were determined from the absorbance at 280 nM based on the molar absorption coefficients for the caspases calculated from the Edelhoch relationship (Edelhoch, 1967); caspase-3 ($e_{280}$=26000 M$^{-1}$ cm$^{-1}$), caspase-9 ($e_{280}$=30010 M$^{-1}$ cm$^{-1}$).

For the results shown in FIG. 7C, pro-caspase-9 was in vitro translated in reticulocyte lysates in the presence of $^{35}$S-L-methionine and then purified by metal chromatography. The resulting samples (2 µl) were either immediately boiled in an equal volume of Laemmli buffer or incubated at 30° C. for 1 hr alone or with 0.1 µM recombinant active caspase-9 in the presence or absence of 0.1 µM GST-XIAP or a GST control protein. Proteins were analyzed by SDS-PAGE and autoradiography. An asterisk denotes the processed form of caspase-9. Recombinant GST control proteins had little or no effect upon caspase-9 activity in these assays.

Example X

XIAP, c-IAP-1 and c-IAP-2 Inhibit Caspase-9 Induced Processing of Pro-Caspase-3 in Intact Cells This example demonstrates that in intact cells, as in in vitro, IAP family proteins can inhibit caspase-9 activity.

In view of the inhibitory effect of XIAP, c-IAP-1 and c-IAP-2 on pro-caspase-9 activation in vitro, IAP family proteins were assayed for the ability to protect against caspase-9-induced apoptosis in intact cells and to inhibit downstream events such as processing of pro-caspase-3. Overexpression of caspases in vivo often results in apoptosis (reviewed in Jacobson and Evan, supra, 1994; Martin et al., supra, 1995; Patel et al., supra, 1996); therefore, to explore the effect of IAPs on caspase-9 activation in vivo, 293T cells were transfected with epitope tagged FLAG-caspase-9 alone or in combination with a myc-tagged IAP. Lysates were collected one day following transfection and the proteolytic processing of pro-caspase-3 examined by immunoblot analysis. As shown in FIG. 8A, overexpression of caspase-9 resulted in complete conversion of the caspase-3 zymogen and an increase in Ac-DEVD-AFC cleavage activity (FIG. 8B). In contrast, caspase-9-induced proteolytic cleavage of pro-caspase-3 and Ac-DEVD-AFC cleavage activity was markedly reduced in 293T cells that had been co-transfected with XIAP, c-IAP-1 or c-IAP-2. The observed inhibition of pro-caspase-3 processing by XIAP, c-IAP-1 or c-IAP-2 was accompanied by a reduction in the number of apoptotic 293T cells (FIG. 8C). The more extensive suppression of DEVD-cleaving activity than of apoptosis can be due to caspase-9-induced protease activation as a consequence of the short half-life of IAP-family proteins.

Figure 8:
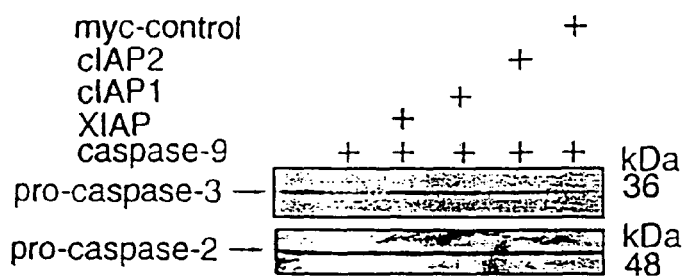
FIG. 8 shows that XIAP, c-IAP-1, c-IAP-2 bind pro-caspase-9 in vivo and inhibit caspase-9 induced processing of caspase-3. 293T cells were transfected with either FLAG tagged pro-caspase-9 or pcDNA-myc-tag control plasmid DNA alone, or in combination with myc-tagged XIAP, c-IAP-1, c-IAP-2 or a myc-tagged control protein. Immunoblot analysis of pro-caspase-3 was performed using lysates from cells induced to undergo apoptosis by overexpressing pro-caspase-9 in the absence or presence of the IAPs. (B) Lysates normalized for total protein content were assayed for hydrolysis of DEVD-AFC. (C) Relative apoptosis determined by DAPI-staining (mean±SE; n=3) for 293 T cells co-transfected with pGFP and FLAG-control (−) or FLAG-pro-caspase-9 (+) and either pcDNA3-myc-tag control plasmid, pcDNA3-myc-XIAP, pcDNA3-myc-IAP-1 or pcDNA3-myc-c-IAP-2. (D) Immunoprecipitation of IAP proteins with anti-myc antibody immobilized on protein G-Sepharose and subsequent immunoblot analysis with anti-FLAG antibody for detection of pro-caspase-9.
Figure 8:
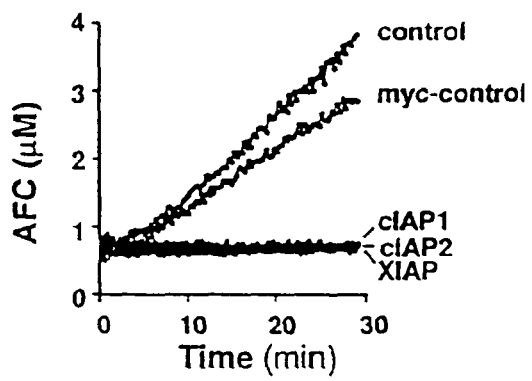
Figure 8:
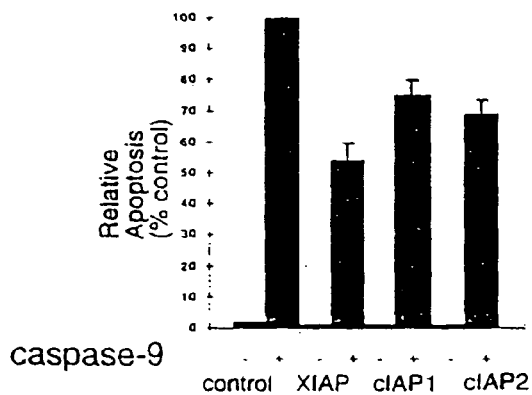
Figure 8:
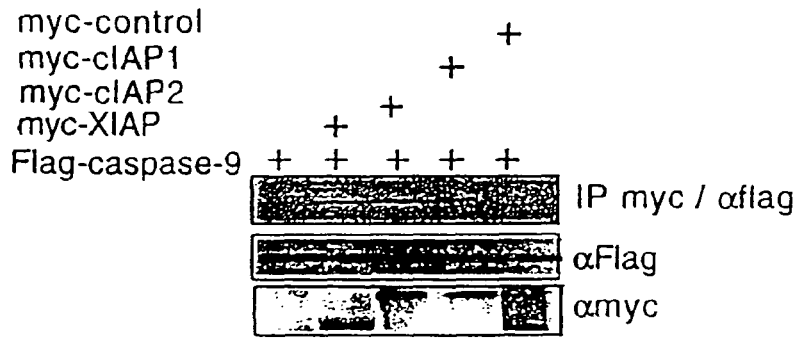

Given that the zymogen form of caspase-9 binds to XIAP, c-IAP-1 and c-IAP-2 in vitro, IAP family proteins were assayed for the ability to bind caspase-9 in vivo. Using 293T cells co-transfected with Flag-pro-caspase-9 and myc-epitope tagged IAP proteins, immunoprecipitations were performed with anti-myc antibody. The resulting immune-complexes were analyzed by immunoblotting using antisera specific for the Flag epitope. As shown in FIG. 8D, the zymogen form of caspase-9 co-immunoprecipitated with XIAP, c-IAP-1 or c-IAP-2 but not with various control proteins (FIG. 8). These results indicate that XIAP, c-IAP-1 and c-IAP-2 each bind to pro-caspase-9 in vivo and prevent its activation, thereby blocking activation of pro-caspase-3 and, consequently, apoptosis.

For the results shown in FIG. 8, 293T cells were transfected with either FLAG tagged pro-caspase-9 or pcDNA-myc-tag control plasmid DNA alone or in combination with myc-tagged XIAP, c-IAP-1, c-IAP-2 or a myc-tagged control protein. Cell lysates were prepared 16 hr later for either (A) immunoblot analysis of caspase-3, or (B) DEVD-AFC.

Immunoblot analysis of pro-caspase-3 was performed with lysates from cells induced to undergo apoptosis by overexpressing pro-caspase-9 in the absence or presence of the IAPs. For DEVD-AFC analysis, lysates were normalized for total protein content and assayed for hydrolysis of DEVD-AFC as described above. Relative apoptosis was scored at 1.5-2 days after transfection by DAPI staining (mean±SE; n=3) for 293 T cells co-transfected with pGFP and FLAG-control or FLAG-pro-caspase-9, and either pcDNA3-myc-tag control plasmid, pcDNA3-myc-XIAP, pcDNA3-myc-IAP-1 or pcDNA3-myc-c-IAP-2. In panel D, IAP proteins were immunoprecipitated with anti-myc antibody immobilized on protein G-Sepharose at ~16 hours post-transfection. Immunoblot analysis with anti-FLAG antibody was employed for detection of pro-caspase-9 in the resulting immune complexes. Lysates from the same cell (50 μg per lane) were also analyzed by immunoblotting using anti-FLAG and anti-myc antibodies to verify expression of IAPs and caspase, respectively.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of identifying an agent that modulates the activation of a caspase by an inhibitor of apoptosis (IAP) protein, comprising the steps of:
   a) contacting in vitro a caspase selected from the group consisting of caspase-3, caspase 7 and caspase-9 and the IAP, wherein the IAP is selected from XIAP, cIAP-1 and c-IAP-2 and wherein the IAP inhibits activation of the caspase, under conditions that allow activation of the caspase in the absence of the IAP, and an agent suspected of being able to modulate caspase inhibitory activity of the IAP; and
   b) detecting caspase activity, wherein caspase activity identifies an agent that modulates the regulation of activation of the caspase by the IAP.

2. The method of claim 1, wherein said IAP is a eukaryotic IAP.

3. The method of claim 2, wherein said eukaryotic IAP is an X chromosome linked IAP (XIAP).

4. The method of claim 2, wherein said eukaryotic IAP is selected from the group consisting of c-IAP-1 and c-IAP-2.

5. The method of claim 1, wherein said caspase is selected from the group consisting of caspase-3, caspase-7 and caspase-9.

6. The method of claim 1, wherein said conditions that allow activation of the caspase in the absence of the IAP are incubation of the caspase in a cytosolic extract containing cytochrome c.

7. The method of claim 1, wherein said conditions that allow activation of the caspase in the absence of the IAP are incubation of the caspase in a cytosolic extract containing caspase-8.

8. The method of claim 1, wherein said caspase activity is detected by proteolysis of a substrate.

9. The method of claim 1, wherein said caspase activity is detected using an antibody.

10. A method of identifying an agent that alters the specific association of a caspase and an inhibitor of apoptosis (IAP) protein, comprising the steps of:
   a) contacting a caspase selected from the group consisting of caspase-3, caspase 7 and caspase-9 and the IAP, wherein the IAP is selected from XIAP, cIAP-1 and c-IAP-2, under conditions that allow the caspase and the IAP to specifically associate, with an agent suspected of being able to alter the association of the caspase and the IAP; and
   b) detecting an altered association of the caspase and the IAP, thereby identifying an agent that alters the association of the caspase and the IAP.

11. The method of claim 10, wherein said contacting is performed in vitro.

12. The method of claim 10, wherein said contacting occurs in a cell.

13. The method of claim 10, wherein said IAP is a eukaryotic IAP.

14. The method of claim 13, wherein said eukaryotic IAP is an X chromosome linked IAP (XIAP).

15. The method of claim 13, wherein said eukaryotic IAP is selected from the group consisting of c-IAP-1 and c-IAP-2.

16. The method of claim 1, wherein the caspase is caspase-3.

17. The method of claim 1, wherein the caspase is caspase-7.

18. The method of claim 1, wherein the caspase is caspase-9.

19. The method of claim 1, wherein the IAP is XIAP.

20. The method of claim 1, wherein the IAP is cIAP-1.

21. The method of claim 1, wherein the IAP is c-IAP-2.

22. The method of claim 10, wherein the caspase is caspase-3.

23. The method of claim 10, wherein the caspase is caspase-7.

24. The method of claim 10, wherein the caspase is caspase-9.

25. The method of claim 10, wherein the IAP is XIAP.

26. The method of claim 10, wherein the IAP is cIAP-1.

27. The method of claim 10, wherein the IAP is c-IAP-2.

* * * * *

SEQUENCE LISTING

```
<160> NUMBER OF SEQ ID NOS: 12

<210> SEQ ID NO 1
<211> LENGTH: 5
<212> TYPE: PRT
<213> ORGANISM: Unknown
<220> FEATURE:
<221> NAME/KEY: SITE
<222> LOCATION: (4)
<223> OTHER INFORMATION: any amino acid
<220> FEATURE:
<223> OTHER INFORMATION: Description of Unknown Organism: Consensus
      Sequence

<400> SEQUENCE: 1

Gln Ala Cys Xaa Gly
  1               5

<210> SEQ ID NO 2
<211> LENGTH: 4
<212> TYPE: PRT
<213> ORGANISM: Unknown
<220> FEATURE:
<223> OTHER INFORMATION: Description of Unknown Organism:Consensus
      Sequence

<400> SEQUENCE: 2

Asp Glu Val Asp
  1

<210> SEQ ID NO 3
<211> LENGTH: 4
<212> TYPE: PRT
<213> ORGANISM: Unknown
<220> FEATURE:
<223> OTHER INFORMATION: Description of Unknown Organism:Consensus
      Sequence

<400> SEQUENCE: 3

Tyr Val Ala Asp
  1

<210> SEQ ID NO 4
<211> LENGTH: 33
<212> TYPE: DNA
<213> ORGANISM: Homo sapiens

<400> SEQUENCE: 4
gggaattcat gacttttaac agttttgaag gat                                  33
```

```
<210> SEQ ID NO 5
<211> LENGTH: 29
<212> TYPE: DNA
<213> ORGANISM: Homo sapiens

<400> SEQUENCE: 5
ctctcgagca tgcctactat agagttaga                                    29

<210> SEQ ID NO 6
<211> LENGTH: 21
<212> TYPE: PRT
<213> ORGANISM: Homo sapiens
<220> FEATURE:
<221> NAME/KEY: MOD_RES
<222> LOCATION: (21)
<223> OTHER INFORMATION: AMIDATION

<400> SEQUENCE: 6

Cys Asp Ala Val Ser Ser Asp Arg Asn Phe Pro Asn Ser Thr Asn Leu
  1               5                  10                  15

Pro Arg Asn Pro Ser
             20

<210> SEQ ID NO 7
<211> LENGTH: 29
<212> TYPE: DNA
<213> ORGANISM: Homo sapiens

<400> SEQUENCE: 7
agggaattca tgcacaaaac tgcctccca                                    29

<210> SEQ ID NO 8
<211> LENGTH: 29
<212> TYPE: DNA
<213> ORGANISM: Homo sapiens

<400> SEQUENCE: 8
ctcctcgagg atggcttcaa gtgttcaac                                    29

<210> SEQ ID NO 9
<211> LENGTH: 31
<212> TYPE: DNA
<213> ORGANISM: Homo sapiens

<400> SEQUENCE: 9
agggaattca tgaacatagt agaaaacagc a                                 31

<210> SEQ ID NO 10
<211> LENGTH: 31
<212> TYPE: DNA
<213> ORGANISM: Homo sapiens

<400> SEQUENCE: 10
ctcctcgaga gatgatgttt tggttcttct t                                 31

<210> SEQ ID NO 11
<211> LENGTH: 37
<212> TYPE: DNA
<213> ORGANISM: Homo sapiens

<400> SEQUENCE: 11
ctcctcgagg atctaacctt gaatctcatc aacaaac                           37
```

```
<210> SEQ ID NO 12
<211> LENGTH: 38
<212> TYPE: DNA
<213> ORGANISM: Homo sapiens

<400> SEQUENCE: 12
ctcctcgagg atctacttga acttgacgga tgatgaac                              38
```